US008073551B2

(12) United States Patent
McCann et al.

(10) Patent No.: US 8,073,551 B2
(45) Date of Patent: Dec. 6, 2011

(54) COIL ELECTRODE APPARATUS FOR THERMAL THERAPY

(75) Inventors: Claire McCann, Toronto (CA); Michael D. Sherar, Toronto (CA)

(73) Assignee: University Health Network, Toronto (CA)

( * ) Notice: Subject to any disclaimer, the term of this patent is extended or adjusted under 35 U.S.C. 154(b) by 1280 days.

(21) Appl. No.: 11/696,550

(22) Filed: Apr. 4, 2007

(65) Prior Publication Data

US 2007/0270924 A1 Nov. 22, 2007

Related U.S. Application Data

(60) Provisional application No. 60/788,696, filed on Apr. 4, 2006.

(51) Int. Cl.
*A61F 7/00* (2006.01)
(52) U.S. Cl. .................. 607/101; 607/102; 606/34
(58) Field of Classification Search ............. 606/32, 606/33, 41, 49, 34; 607/101–102
See application file for complete search history.

(56) References Cited

U.S. PATENT DOCUMENTS

| 4,494,539 | A | * | 1/1985 | Zenitani et al. ............... 606/33 |
|---|---|---|---|---|
| 5,246,438 | A | | 9/1993 | Langberg |
| 5,364,392 | A | | 11/1994 | Warner et al. |
| 5,470,352 | A | | 11/1995 | Rappaport |
| 5,507,743 | A | | 4/1996 | Edwards et al. |
| 5,536,267 | A | | 7/1996 | Edwards et al. |
| 5,672,173 | A | * | 9/1997 | Gough et al. ............... 606/41 |
| 5,817,092 | A | | 10/1998 | Behl |
| 5,871,523 | A | | 2/1999 | Fleischman et al. |
| 6,050,992 | A | | 4/2000 | Nichols |
| 6,071,280 | A | | 6/2000 | Edwards et al. |
| 6,090,105 | A | | 7/2000 | Zepeda et al. |
| 6,358,246 | B1 | | 3/2002 | Behl et al. |
| 6,471,698 | B1 | | 10/2002 | Edwards et al. |
| 6,632,223 | B1 | | 10/2003 | Keane |
| 6,911,019 | B2 | * | 6/2005 | Mulier et al. ............... 604/114 |
| 6,949,096 | B2 | | 9/2005 | Davison et al. |
| 7,070,595 | B2 | * | 7/2006 | Ormsby et al. ............... 606/33 |
| 2001/0031906 | A1 | | 10/2001 | Ishikawa et al. |

(Continued)

FOREIGN PATENT DOCUMENTS

WO 96/04860 A1 2/1996

(Continued)

OTHER PUBLICATIONS

Beaugrand M, N'Kontchou G, Seror O, Ganne N and Trinchet JC, Local/Regional and systemic treatments of hepatocellular carcinoma. Seminars of Liver Disease. 2005. 25, 201-211.

(Continued)

*Primary Examiner* — Roy Gibson
(74) *Attorney, Agent, or Firm* — Bereskin & Park LLP/S.E.N.C.R.L., s.r.l.

(57) ABSTRACT

A single-coil RF electrode, along with an associated method of operation, has been developed for use in an RF applicator, RFA apparatus or RFA system for heating tumors, including large tumors with a single heating session. The RF electrode generally has a helical geometry, although many variations exist, and is provided with an excitation current having a frequency that is sufficient for magnetic induction and coupling of various electric and magnetic fields to produce an electric field within the volume surrounded by the coil for directly applying heat to the tissue therein.

33 Claims, 22 Drawing Sheets

U.S. PATENT DOCUMENTS

| | | | | |
|---|---|---|---|---|
| 2004/0153120 | A1* | 8/2004 | Seifert et al. | 606/200 |
| 2005/0192654 | A1* | 9/2005 | Chanduszko et al. | 607/116 |
| 2005/0205566 | A1 | 9/2005 | Kassayan | |

FOREIGN PATENT DOCUMENTS

| | | |
|---|---|---|
| WO | 96/029946 | 10/1996 |
| WO | 2004/100812 A1 | 11/2004 |

OTHER PUBLICATIONS

Brezovich IA, Young JH and Wang MT, Temperature distributions in hyperthermia by electromagnetic induction: A theoretical models for the thorax. Medical Physics. 1983. 10 57-65.

Burdio F, Guemes A, Burdio JM, Navarro A, Sousa R. et al, Large Hepatic Ablation with Bipolar Saline-Enhanced Radiofrequency: AN Experimental Study in in Vivo Porcine Liver with a Novel Approach. Journal of Surgical Research. 2003 vol. 110 pp. 193-201.

Chiba T, Tokuuye K, Matsuzaki Y, Sugahara S, Chuganji Y, Kagei K, Shoda J, Hata M, Abei M, Igaki H, Tanaka N and Akine Y, Proton Beam Therapy for Hepatocellular Carcinoma: A retrospective review of 162 patients. Clinical Cancer Research, 2005. 11, 3799-3805.

Chin L and Sherar M, Changes in dielectric properties of ex-vivo bovine liver at 915 MHz during heating, Physics in Medicine and Biology. 2001.46 197-211.

Chute FS and Vermeulen FE, A Visual Demonstration of the Electric Field of a Coil Carrying a Time-Varying Current. IEEE Transactions on Education. 1981. E-24 278-283.

Crowley JD, Shelton J, Iverson AJ, Burton MP, Dalrymple NC and Bishoff JT, Laparoscopic and computed-tomography-guided percutaneous radiofrequency ablation of renal tissue: acute and chronic effects in an animal model. Urology. 2001. vol. 57 pp. 976-980.

Duerig TW, Melton KN, Stöckel D, Wayman CM, Engineering Aspects of Shape Memory Alloys. Butterworth-Heinemann Ltd., Toronto, © 1990, 1-35, 115-136, 193-206, 256-266, 394-413.

Elkamchouchi HM and Salem AL, Helical Antennas with nonuniform diameter. Eighteenth National Radio Science Conference. Mar. 2001. 143-152.

Guerquin-Kern JL, Hagmann MJ, Levin RL, Experimental Characterization of Helical Coils as Hyperthermia Applicators. IEEE Transactions on Biomedical Engineering. 1988. BME-35 46-52.

Iskander M F and Tumeh A M, Design optimization of interstitial antennas. IEEE Transactions on Biomedical Engineering, 1989. 36 238-246.

Jemal A, Murray T, Ward E, Samuels A, Tiwari RC, Ghafoor A, Feuer EJ and Thun MJ, Cancer Statistics 2005, CA Cancer J Clin, 2005. 55 10-30.

Jordan EC and Balmain KG, Electromagnetic Waves and Radiating Systems 2nd Ed. Prentice-Hall, Inc. © 1968, NJ. 100-110, 126-130, 136-139.

Knoepfel H, Magnetic fields: a comprehensive theoretical treatise for practical use. Wiley © 2000, Toronto. 91-125, 201, 202.

Kong FM, Ten Haken RK, Schipper MJ, Sullivan MA, Chen M, Lopez C, Kalemkerian GP and Hayman JA, High-dose radiation improved local tumor control and overall survival in patients with inoperable/unresectable non-small-cell lung cancer: Long-term results of a radiation dose escalation study, Int. J. Radiation Oncology Biol. Phys. 2005. 63 No. 2 324-333.

Kumaradas JC and Sherar MD, An edge-element based finite element model of microwave heating in hyperthermia: method and verification. International Journal of Hyperthermia. 2002. 18 426-440.

Lagerwaard FJ, Senan S, Van Meerbeck JP, Graveland WJ, Has 3-D conformal radiotherapy (3D CRT) improved the local tumor control for stage I non-small cell lung cancer? Radiotherapy & Oncology. 2002. 63 151-157.

Lorrain P and Corson D, Electromagnetic Fields and Waves. W. H. Freeman and Company, © 1962, New York. 276-286, 298-299, 308-319, 332-339, 342-351, 422-425.

Mcgahan JP and Dodd GD, Radiofrequency Ablation of the Liver: Current Status. AJR. 2001. 176 3-16.

McLoud TC, Lung Cancer: Imaging techniques for diagnosis and staging of lung cancer, Clinics in Chest Medicine, 2002. 23 No. 1 123-136.

McDonald, M, Lochhead S, Chopra R and Bronskill MJ, Multimodality tissue-mimicking phantom for thermal therapy. Physics in Medicine and Biology. 2004. 49 2767-2778.

Moore LE, Wilson RT and Campleman SL, Lifestyle factors, exposures, genetic susceptibility, and renal cell cancer risk: a review. Cancer Invest 2005. 23 240-255.

Mountain CF, Revisions in the international system for staging lung cancer. Chest, 1997. 11 1710-1717.

Namjoshi KV and Biringer PP, Multiple conductor induction problem: Analytical approach. American Institute of Physics. 1990. 67 4732-4734.

Namjoshi KV and Biringer PP, Multiple conductors in transverse magnetic field and their application in magnetic shielding. IEEE Transactions on Magnetics. 1991.27 3916-3919.

Rendon RA, Gertner MR, Sherar MD, Asch MR, Kachura JR, Sweet J and Jewett MAS, Development of a radiofrequency based thermal therapy technique in an in-vivo porcine model for the treatment of small renal masses. The Journal of Urology. 2001. 166 292-298.

Ryan TP, Mechling JA and Strohbehn JW, Absorbed power deposition for various insertion depths for 915 MHz interstitial dipole antenna arrays: experiment versus theory. Int J Radiation Oncology Biol. Phys. 1990. 19 377-387.

Ryff PF, Current Distribution in Helical Solenoids, IEEE Transactions on Industry Applications. 1972. 8 485-490.

Stöckel D, Nitinol Medical Devices and Implants. SMST-2000 Conference Proceedings, 2001, 531-541.

Stuchly MA and Stuchly SS, Coaxial Line Reflection methods for Measuring Dielectric Properties of Biological Substances at Radio and Microwave Frequencies—A review. IEEE Trans. Instrum. Meas. 1980. 176-183.

Stuchly MA and Stuchly SS, Measurement of Radio Frequency Permittivity of Biological Tissues with an Open-Ended Coaxial Line : Part I. IEEE Transactions on Microwave Theory and Techniques. 1982. 30 82-86.

Stuchly MA and Stuchly SS, Dielectric Properties of Biological Substances-Tabulated. Journal of Microwave Power. 1980.15 20-25.

Tamaki K, Shimizu I, Oshio A, Fukano H, Lnoue H et al. Influence of large intrahepatic blood vessles on the gross and histological characteristics of lesions produced by radiofrequency ablation in a pig liver model. Liver International. 2004. vol. 24 pp. 696-701.

Wright AS, Sampson LA, Warner TF, Mahvi DM, Lee FT, Radiofrequency versus Microwave Ablation in a Hepatic Porcine Model. Radiology. 2005. vol. 236 pp132-139.

Varkarakis IM, Allaf ME, Lnagaki T, Bhayani SB, Chan DY, Su LM, Jarrett TW, Kavoussi LR and Soloman SB, Percutaneous radio frequency ablation of renal masses: results at a 2 year mean follow-up. The Journal of Urology, 2005. 174 456-460.

International Search Report and Written Opinion for corresponding international application no. PCT/CA2007/000547, date of mailing Jul. 23, 2007.

NDC Nitinol Devices & Components, Nitinol SE508 Wire Material Data Sheet, California NDC: Feb. 2002 (http://www.nitinol.info/pdf_files/se508_wire_data.pdf).

US 6,648,882, 11/2003, Behl et al. (withdrawn)

* cited by examiner

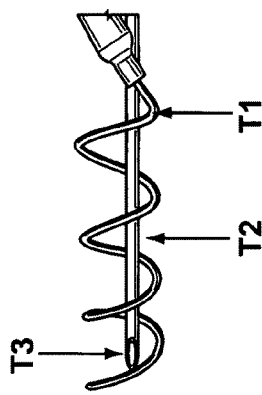
FIG. 26
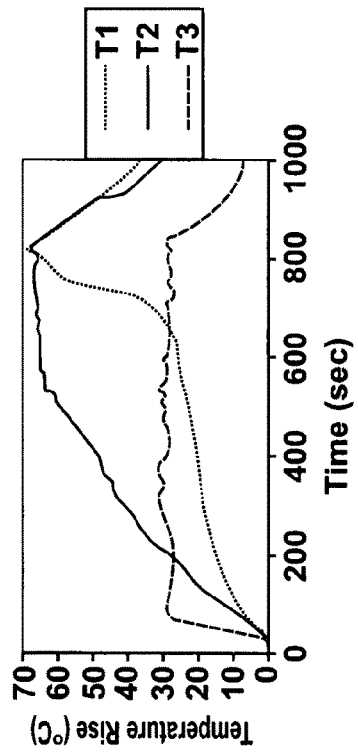
FIG. 28
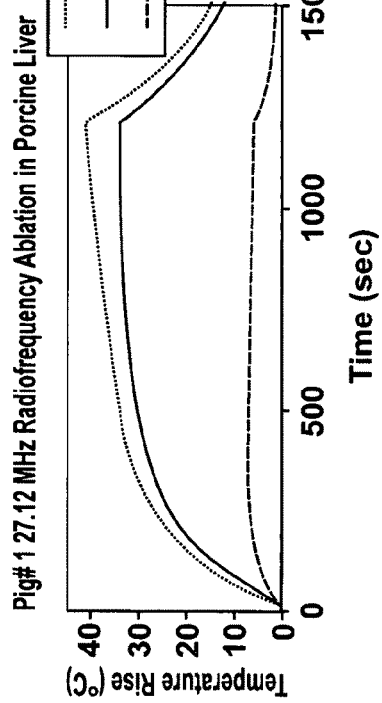

COIL ELECTRODE APPARATUS FOR THERMAL THERAPY

CROSS-REFERENCE

This application claims priority from U.S. Provisional Application Ser. No. 60/788,696 filed on Apr. 4, 2006.

FIELD

Various embodiments are described herein that relate to a coil electrode that can be used to heat tissue.

BACKGROUND

The majority of cancerous tumors in humans occur in the lung, liver and kidney, with the majority of the tumors being solid. Lung cancer, specifically non-small cell lung cancer is a leading cause of cancer death in North America (Jemal et al 2005, McLoud 2002). Liver cancer or hepatocellular carcinoma, is another leading cause of cancer death affecting 1 million people worldwide with 5 year survival as low as 10% (Chiba et al 2005). In addition, Renal Cell Carcinoma (RCC), the most common form of kidney cancer, accounts for 31,000 new cases of cancer diagnosed each year in the U.S. (Moore et al 2005). In fact, the incidence of renal tumors is increasing as improvements in diagnostic imaging have lead to the increasing discovery of small renal masses less than 3 cm in diameter.

The majority of lung and liver cancer patients are diagnosed at an advanced stage of the disease, often with large tumors exceeding 3 cm in diameter (McLoud 2002; Beaugrand et al 2005), which have either been shown to have a high incidence of local recurrence following standard radiotherapy techniques or 3D conformal radiotherapy (Lagerwaard et al 2002), or cannot be resected. The treatment of choice for RCC is partial or complete surgical removal of the kidney, however the rising incidence and increased detection of small renal masses have stimulated interest in developing less radical therapeutic alternatives (Varkarakis et al 2005, Rendon et al 2001).

In the treatment of solid tumors the two main issues to contend with are pain management, and inhibition of tumor growth. Current treatments of tumors tend to address one or the other issue. These treatments include surgery, chemotherapy, cryosurgery, ethanol injection, radiation therapy, and interstitial thermal therapy.

Surgery is considered to be the "gold standard" in the treatment of liver tumors. However, 70 to 90% of liver cancer patients are unresectable, meaning that they do not qualify for surgery because of limited liver function and/or unfavourable anatomy. Generally, about 15% of the patients with tumors less than 2 cm are amenable to resection. The few patients who do qualify for surgery have a 2% mortality rate and cannot be re-operated on in the likely occurrence of tumor regrowth. For lung cancer, surgery is the treatment of choice, with 5-year survival rates of 50-70% (Mountain 1997). However, only 20% of lung cancer patients are amenable to this procedure. Furthermore, in general, surgery typically limits organ function afterwards.

Chemotherapy has also been used locally and systemically for treatment of liver cancer tumors. However, there is an increase in pain for the patient as well as significant side effects such as vomiting, ulcerations and risk of infection. Chemotherapy inhibits tumor growth but generally is not an effective treatment because of excessive toxicity and lack of survival benefit.

In cryosurgery, steel probes are used to deliver liquid nitrogen to freeze the tumor. However, the freeze-thaw cycle of this procedure may cause organ damage or hemorrhaging to the organ that contains the tumor. For instance, with liver tumors, cryosurgery inhibits the tumor but weakens the liver. Furthermore, cryosurgery is not an option for non-resectable tumors, and multiple treatments are generally required.

Percutaneous ethanol injection involves injection of alcohol into the tumor. This procedure requires multiple treatments and may lead to pain. Furthermore, this procedure can weaken the organ that contains the tumor, is ineffective on large tumors and multiple treatments are usually required.

Radiation therapy is infrequently used in the treatment of liver cancer. It is not effective and can actually be more harmful to the patient, causing radiation hepatitis and death. Meanwhile, when radiation therapy is used with patients having lung tumors that are non-surgical candidates, 10-34% of these patients survive to 5 years depending on the stage of the disease (Kong et al 2005). For those patients with locally advanced unresectable disease treated with radiotherapy alone, 5-year survival is less than 10%, with 45% of patients having isolated local failure.

Interstitial thermal therapies have been developed to improve local tumor control in a minimally invasive manner using heat in the range of 50°-90° C. Interstitial applicators are delivered through laparoscopy or percutaneously, and localize thermal energy to the target volume. A variety of non-ionizing energy sources are currently used for interstitial thermal therapy including laser, microwave, ultrasound and radio frequency (RF) energy. Laser-induced interstitial thermotherapy uses light to thermally coagulate small (<2 cm), solid tumors. Microwave thermal therapy typically uses energy at frequencies of 433, 915 and 2450 MHz to heat and coagulate tissue. Interstitial ultrasound uses high intensity acoustic energy in the range of 2 MHz-10 MHz to thermally coagulate tissues.

RF thermal therapy, also known as RF ablation (RFA), is a relatively new treatment that is minimally invasive and so can be used on patients where open surgery is contraindicated. Moreover, unlike other treatments, RFA has thus far proven to be unhampered by many of the above-mentioned limitations of conventional treatments and repeat RFA treatments can be administered without toxicity. There is no known contraindication for the use of RFA before or after treatments. RFA can also be used in conjunction with other therapies. Clinically, RFA has been approved or is under investigation for a range of malignancies in liver, bone, lung and kidney.

RFA conventionally uses RF energy in the range of 460-500 KHz to elevate temperatures sufficient to induce coagulative necrosis. Examples of RF applicators include monopolar needle electrodes and retractable curved electrodes having an umbrella shape, which require an external ground plane to complete the current path. In RFA therapy, the metal electrode is inserted into the tumor and is heated to 55-90° C. by a radio frequency driving current. Thermal conduction is then used to 'spread' the heat throughout the tumor. However, heat sinks, such as perfusion for example, limit the effectiveness of this heat transfer mechanism. For instance, renal ablation studies in porcine models by Rendon et al. (2001) indicated that lesion size was not reproducible due to renal blood flow, which limited therapeutic heating within the boundaries of the umbrella electrode that was used.

Furthermore, conventional RFA technology suffers from small, non-uniform, heating fields when using single interstitial therapy applicators. For instance, the needle electrodes produce small volumes of coagulated tissue, typically 1-2 cm in diameter, while the umbrella electrode produces at most, a 3 cm diameter ablation (McGahan and Dodd 2001). In the liver, Varkarakis (2005) showed that large (>3 cm) renal tumors were difficult to treat with conventional RF ablation and had a tendency for recurrence. In fact, McGahan and Dodd recommended that the largest tumor that should be treated by a single RF ablation electrode should be smaller than 2 cm in diameter. Larger tumors (>3 cm in diameter) require an array of applicators or multiple insertions of a single applicator in order to heat the whole tumor to cytotoxic levels, resulting in a more invasive procedure. Also, the ability to generate a uniform treatment field throughout a large target volume, necessary for local tumor control, is difficult when multiple applicators are used simultaneously, or when the tumor is highly vascular.

SUMMARY

In one aspect, at least one embodiment described herein provides an apparatus for heating a target tissue region. The apparatus comprises: a control unit for controlling the operation of the apparatus, the control unit including a user interface adapted for allowing a user to use the apparatus; a signal generator coupled to the control unit, the signal generator being adapted for generating an excitation current having a frequency in the range of about 5 to 50 MHz; a power amplifier coupled to the signal generator for amplifying the excitation current; an impedance matching circuit coupled to the power amplifier for reducing impedance mismatch; and an applicator coupled to the impedance matching circuit, the applicator including a single, helical coil electrode for application to the target tissue to heat the target tissue when provided with the excitation current.

In another aspect, at least one embodiment described herein provides a method of heating a target tissue region of a patient. The method comprises: applying a single, helical coil electrode at the target tissue region; generating an excitation current with a frequency sufficient for magnetic induction to generate an axial electric field within the volume surrounded by the coil electrode; and applying the excitation current to the coil electrode.

In another aspect, at least one embodiment described herein provides an electrode arrangement for heating a target tissue region of a patient. The electrode arrangement comprises a single coil electrode for application at the target tissue region, wherein the coil electrode is adapted to produce an axial electric field within the volume surrounded by the coil electrode when provided with an excitation current having a frequency in the range of 5 to 50 MHz.

In another aspect, at least one embodiment described herein provides an electrode arrangement for heating a target tissue region of a patient. The electrode arrangement comprises a single coil electrode having a helical geometry and arranged to be operated with a time-varying current source at a frequency sufficient for magnetic induction, the time-varying current source produces a circumferential electric field and a secondary axially directed electric field, within the volume surrounded by the coil electrode, the secondary axially directed electric field arising from the charge distribution along the coil electrode.

In another aspect, at least one embodiment described herein provides for use of an electrode arrangement as defined above for heating tissue.

BRIEF DESCRIPTION OF THE DRAWINGS

For a better understanding of the various embodiments described herein, and to show more clearly how they may be carried into effect, reference will now be made, by way of example only, to the accompanying drawings which show at least one exemplary embodiment and in which:

FIG. 26 is an illustration of an RF coil electrode used for in-vivo porcine experiments;

FIG. 28 shows plots showing temperature rise measured in real-time during a 27.12 MHz radiofrequency ablation procedure of normal porcine liver (left) and kidney tissue (right).

DETAILED DESCRIPTION

Figure 1A:
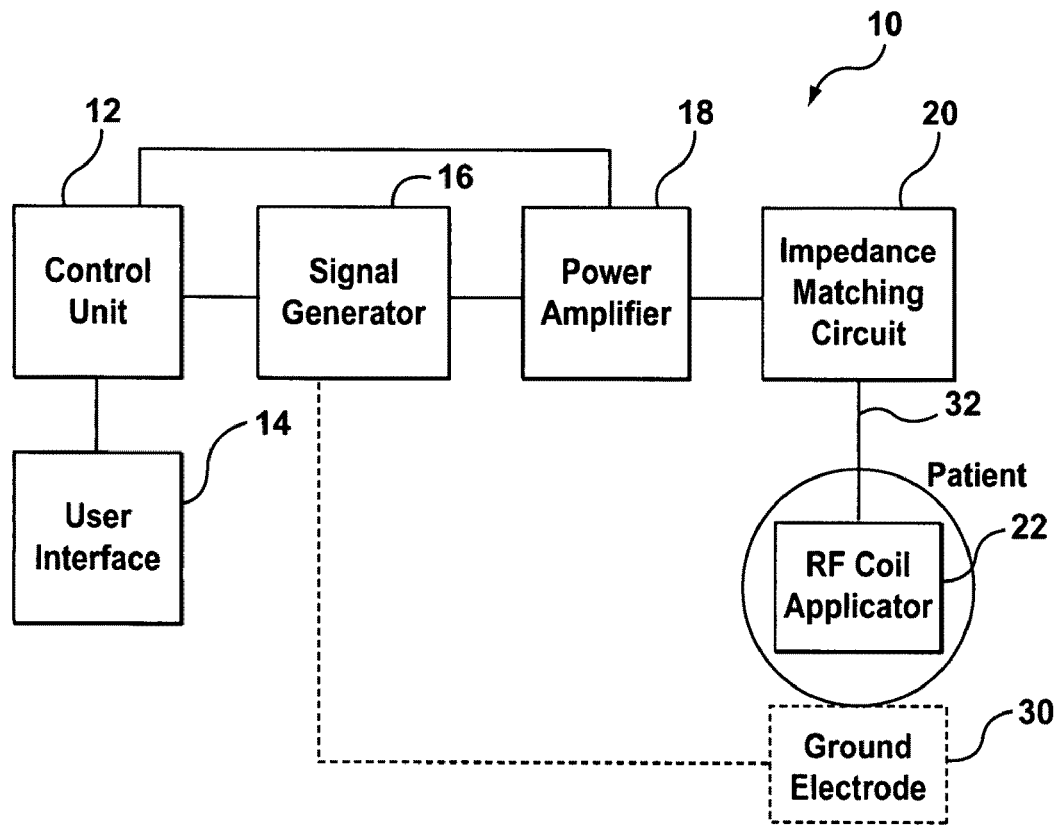
FIGS. 1a and 1b show a block diagram of an exemplary embodiment of an RF tissue ablation apparatus.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

An RF electrode, along with an associated method of operation, has been developed for use in an RF applicator, RFA apparatus or RFA system for heating tumors, including large tumors with a single heating session. The RF electrode can be a single coil electrode generally having a helical geometry, although the RF electrode can have alternative geometries in alternative embodiments. The single coil electrode is applied to a tissue target region and is provided with an excitation current having a frequency that is sufficient for magnetic induction and coupling of various electric and magnetic fields to produce an electric field within the volume surrounded by the coil that is not restricted to the conducting wire itself as is the case for conventional RF electrodes that are provided with an excitation current having a frequency of 460-500 kHz. Such an electric field within the volume surrounded by the RF coil electrode, as described herein, can deliver uniform heat and produce large therapeutic SAR patterns capable of creating large zones of coagulative necrosis for tumors such as those of the liver, kidney and lung. This can be done with improved local control and in a minimally invasive fashion, thereby preserving surrounding healthy tissues, and can be applied to large tumors ($\geq$3 cm). The RF coil electrodes and method of operation described herein can be applied to a variety of tissues, including but not limited to, lung, liver, kidney, muscle and breast tissue.

Figure 1B:
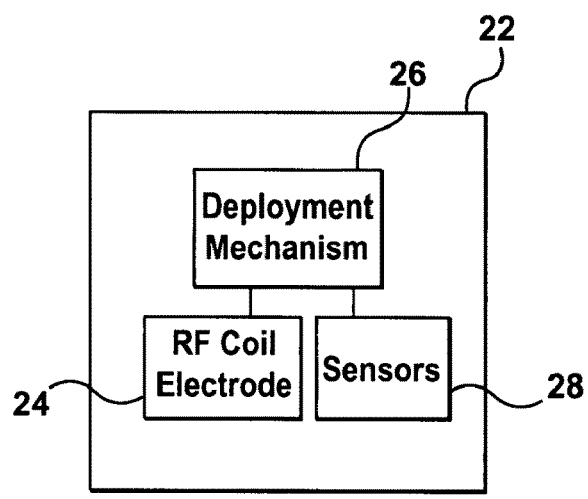

Referring now to FIGS. 1a and 1b, shown therein is a block diagram of an exemplary RF tissue ablation apparatus 10. The apparatus 10 includes a control unit 12, a user interface 14, a signal generator 16, a power amplifier 18, an impedance matching circuit 20, and an RF coil applicator 22. The RF coil applicator 22 includes a coil electrode 24, a deployment mechanism 26, and one or more sensors 28. Depending on the configuration of the electrode 24, the apparatus 10 can additionally (optionally) include a ground electrode 30. The apparatus 10, and more particularly the coil electrode 24, and the associated method of operation described herein can be applied to a variety of tissues, including but not limited to, lung, liver, kidney, muscle and breast tissue.

The apparatus 10 can be a standalone device with elements 12-20 provided in a common housing with a cable 32 connecting the impedance matching circuit 20 to the RF coil applicator 22. In this case, the apparatus 10 can also include a power supply along with voltage regulation circuitry (both not shown but are well known to those skilled in the art) for providing power to the various components of the apparatus 10. Alternatively, the apparatus 10 can be configured in a distributed fashion with components 12-20 being provided by physically separate elements that are connected with cables (in this case cable 32 is still required). In this case, one or more of these components can include their own internal power supply. Furthermore, in this case, the control unit 12 and user interface 14 may not be needed since the components 16, 18 and 20 can each include a user interface for controlling the operation of these components as well as a visual indicator, such as a display or printed labels for associated control dials, to indicate the operational settings of these components.

The control unit 12 controls the operation of the apparatus 10 and allows a user, such as a medical practitioner, to use the apparatus 10 to heat tumor tissue for a patient by specifying values for operational parameters using the user interface 14. The patient can be a human or an animal. The control unit 12 can be implemented using a suitable controller or microprocessor as is commonly known by those skilled in the art. The user interface 14 has an input means (not shown) which can include one or more of a keypad, a keyboard, dials, rotary or slide switches, a touch sensitive screen, a mouse and the like that can be used by the user to provide input to the apparatus 10. The user interface 12 can also include a display that can provide feedback to the user, such as graphical or visual display, for example, of the operating parameters of the apparatus 10.

The user can provide input to the apparatus 10 for setting the operational parameters of the apparatus 10. These operational parameters can include the frequency of the excitation current that is generated by the signal generator 16, the power of the excitation current that is applied to the RF coil applicator 22, the length of time for which the excitation current is applied to the RF coil applicator 22, the size and location of the tumor, as well as other parameters. The operational parameters can also include safety parameters such as a critical temperature that can be used to disable the operation of the apparatus 10 when the temperature of the RF coil applicator 22 exceeds a certain temperature limit.

The signal generator 16 receives control signals from the control unit 12 to generate an excitation current signal that is applied to the RF coil applicator 22, after amplification and waveform processing, to generate electric fields that are used to heat the tumor tissue. The signal generator 16 can be considered to be a time-varying current source. The frequency range of the excitation current signal is preferably in the range of 5 to 50 MHz, although this range may be extendable in some cases. The nature of the electric fields that are desired is discussed in more detail below.

The power amplifier 18 amplifies the excitation current signal to a desired level, which can be on the order of 20 to 500 Watts. For heating tissue in environments with little or no perfusion, power levels as low as 30-40 Watts can be effective, while heating tissue in highly perfused environments, such as the kidney or liver, can require the applied power to be as much as 200 Watts. A sufficient amount of gain is applied to the excitation current signal so that the large solid tumors are preferably heated to the range of 50°-90° C. The amount of amplification can be varied depending on the size of the tumor that is to be treated such that the RF coil applicator 22 can produce a sufficiently large coagulation volume in a single treatment stage. For instance, larger tumors or tumors in highly perfused regions may require a higher heating power from the applicator 22. Accordingly, the power amplifier 18 can be a variable gain amplifier.

The impedance matching circuit 20 processes the amplified excitation current signal for maximum power delivery to the RF coil applicator 22. Accordingly, the impedance matching circuit 20 includes circuitry for matching the impedance of the cable 32, the RF coil applicator 22 itself, as well as the tissue in which the RF coil applicator 22 is applied. The length of the cable 32 also has an effect on the impedance matching circuit 20. The configuration of the impedance matching circuit 20 does not have to be appreciably changed when the RF coil applicator 22 is applied to liver tissue, kidney tissue or lung tissue. The impedance matching circuit 20 can be implemented using a network of inductors and capacitors, as is commonly known by those skilled in the art. The impedance matching circuit 20 can also include a transformer. In one exemplary embodiment, the impedance matching circuit 20 includes a capacitor and inductor connected in series that are used to eliminate the reactive component of the impedance seen downstream from the circuit 20, i.e. to achieve resonance. A step-down transformer, is connected in series with the capacitor and inductor to match the resistive component of the tissue-loaded coil system to the signal generator 16.

In use, the RF coil applicator 22 can be inserted into the tissue of the patient at the site of the tumor. The deployment mechanism 26 is used to deploy the RF coil electrode 24 into the tumor once the RF coil applicator 22 has been positioned near the tumor. Various imaging modalities can be used to position the RF coil applicator 22 near the tumor, as is commonly known by those skilled in the art. These imaging modalities include fluoroscopy, magnetic resonance imaging, 3-dimensional cone beam computer tomography and the like. The imaging modalities can also be used to assess therapeutic response following heating of the tissue tumor. Further, various deployment mechanisms can be used that can be actuated to insert the RF coil electrode 24 into the tumor as is commonly known by those skilled in the art. The sensors 28 can be optional but if used can include temperature sensors, such as a fluoroptic temperature sensor for example, to measure the temperature increase in the tissue during use. In addition, there can be alternative embodiments, which do not include a housing or a deployment mechanism for the RF coil electrode 24. In these cases, the RF electrode 24 can be manually slid down a non-conducting channel to the location of the tumor tissue that is to be heated. Alternatively, there can be some situations in which the RF electrode 24 can be directly applied to a tissue target region. For instance, open insertion is also possible, such as in laparotomystyle in which the abdomen is opened, and the coil electrode 24 can be inserted directly into the organ to heat a tissue target region.

The RF coil applicator 22 can generally be considered to house an electrode arrangement that includes a single coil electrode 24 that is applied to the target tissue site. This is in contrast to conventional devices, which apply two or more electrodes to the target tissue site. Various geometries can be selected for the RF coil electrode 24 that is used in the applicator 22 (for example, see FIGS. 2b-3b, 7, 20, 22 and 24). The RF coil electrode 24 generally has a helical shape and can be implemented with a loosely wound coil, a more tightly wound coil, a tapered coil, and variations thereof. The generated electric fields are better for a tightly wound coil, since it has more turns, but in certain situations such a coil provides more trauma to the tissue and is harder to deploy. A loosely wound coil can more easily be inserted into a tumor tissue for interstitial use. In general, the size and configuration of the RF coil electrode 24 can be selected to match the size of the tumor to be treated and the operating frequency can then be adjusted, based on the size of the RF coil electrode 24 and the coil configuration (i.e. monopolar vs. bipolar), to achieve the desired electric fields within the volume surrounded by the RF coil electrode 24. Alternatively, given a sufficient operating frequency, the size of the RF coil electrode 24 can be selected to generate such electric fields. Selection of coil parameters can also depend on the use of a bipolar or monopolar coil configuration. For example, for a 27.12 MHz excitation current, a bipolar RF coil electrode with a length and diameter comparable to the tumor size (1-5 cm diameter tumor) and a pitch less than or about 1.5 cm may be used. For use of monopolar coils, tumors of various sizes can be treated provided an aspect ratio of 2-4 is maintained with corresponding changes in frequency necessary to maintain a certain range of electrical lengths, such as, but not limited to about 20-25% of the wavelength of the excitation current although this number may change under certain circumstances. The point is to use an electrical length that ensures a reasonable uniform current across the coil length. The electrical length is defined as the physical coil wire length divided by the wavelength of the operating frequency in the tumor tissue. The electrical length can be calculated differently depending on configuration. For example, for a bipolar coil configuration, the electrical length depends on just the coil wire length but in the monopolar coil configuration, the electrical length depends on coil wire length plus the distance to a ground plane. The coil electrode 24 may also include a sharpened tip for insertion into the target tissue.

Generally, the geometry of the RF coil electrode 24 and the frequency of the excitation current are selected such that a uniform axially directed magnetic field is generated within the RF coil electrode 24, which when time varying, results in an electric field inside the RF coil electrode 24, which lies mainly in the circumferential direction. In addition to this magnetically induced electric field, there also exists an axially directed electric field inside the RF coil electrode 24. The design of the RF coil electrode 24 and the operating frequencies that are used exploit the size and uniformity of these electric fields, for heating and coagulating a large tissue volume within the volume surrounded by a single RF applicator 22. Accordingly, the coil electrode 24 can be selected having a centimeter-sized helical geometry operated with a time-varying current source at a frequency sufficient for magnetic induction, which produces a circumferential electric field, and a secondary axially directed electric field which arises from the charge distribution along the coil conductor.

The frequency of the excitation current is preferably in the tens of MHz and is preferably within the range of 5 to 50 MHz, although in some cases other frequencies may be used provided that electric and magnetic fields can be generated as described herein. The specific frequency that is used depends on the geometry and size of the RF coil electrode 24 and whether the coil configuration is bipolar or monopolar, which is discussed further below. Generally, the RF coil electrode 24 can have a length of 1 to 6 cm, a diameter of 0.5 to 3 cm, and a pitch of 0.5 to 2 cm (pitch is defined as coil length divided by the number of turns). The coil electrode 24 can have a major dimension that is at least 50% larger than the minor dimension. The coil electrode 24 can have an aspect ratio of about 2 to 4. The aspect ratio is defined as the coil length divided by the coil diameter. The coil electrode 24 can have a wire thickness of about 0.5 to 1.25 mm. However, all of these dimensions can change depending on the operating frequency. The length of the wire that is used in the RF coil electrode 24 is a parameter that affects the type of fields that are produced. One example of a coil geometry for the RF coil electrode 24 is a loosely wound, helical coil having a length of 4 cm, a diameter of 2 cm and a pitch of 1 cm that is operated at a frequency of about 27 MHz. Such an RF coil electrode can be used to treat large tumors (>3 cm).

As a general rule of thumb, by exploiting the relationship between the coil electrode dimensions and the operating frequency, tumors of various sizes can be treated by a single, loosely wound, helical electrode coil provided with an excitation current having an appropriate frequency. The operating frequency is chosen to be sufficient enough to promote magnetic induction but low enough to minimize the effects of the opposing induction fields set up by the induced eddy currents.

It is also desirable to have good electrical coupling between the tumor and the RF coil electrode 24 so that the energy of the generated electric fields is optimally transferred to heat the tumor. The interstitial insertion of the RF coil applicator 22 into the tissue provides a good coupling provided that there are no air gaps between the RF coil electrode 24 and the tumor, since this will reduce the strength of the generated electric fields. Further, operation of a loosely wound tumor-sized coil at radio frequencies, as described herein, results in a current path length that is much less than the wavelength of the RF signal applied to the coil electrode. This latter condition produces axial fields that are essentially uniform throughout the length of the coil electrode.

The RF coil electrode 24 can be constructed from a shape memory, electrically conductive alloy to allow for the percutaneous deployment of the RF coil electrode into a tumor tissue in a minimally invasive fashion. An example of a shape memory alloy that can be used is Nitinol, which is a nickel and titanium alloy. Nitinol has an electrical conductivity similar to that of stainless steel, is MR compatible, biocompatible, and has very high corrosion resistance (Stöckel 2001).

The procedure to make an RF coil electrode is now discussed. This procedure can be adapted to make coil electrodes having different lengths, diameters, pitches, and number of turns using conductors having various diameters and current ratings. The particular values used for the parameters of the RF coil electrode will depend on the nature of the tumor that is to be treated, and the power and RF frequency range of the excitation current that will be applied to the RF coil electrode.

For one exemplary RF coil electrode, a straight, 1.25 mm diameter round wire sample of Nitinol (NDC-Nitinol Devices & Components, Fremont, Calif., USA) can be wound onto a 2 cm diameter cylindrical mandrel with a 1 cm pitch helical groove cut into the fixture. The wire/fixture assembly can then be heat treated in an annealing oven (TLD Annealing Furnace, Radiation Products Design, Inc. Albertville, Minn., USA) for 10 minutes at an average temperature of 500° C. After heating, the coil/fixture assembly is rapidly quenched in ice water. This heat treatment procedure is designed to produce a superelastic coil, whereby mechanical deformation of the coil above its transformation temperature (i.e. Austenite finish temperature $A_f$) causes a stress-induced phase transformation from Austenite to Martensite. The stress-induced Martensite is unstable at temperatures above $A_f$ so that when the stress is removed, the Nitinol will immediately spring back to the Austenite phase and its pre-stressed shape (Duerig et al 1990, Stöckel 2001).

Figure 2A:
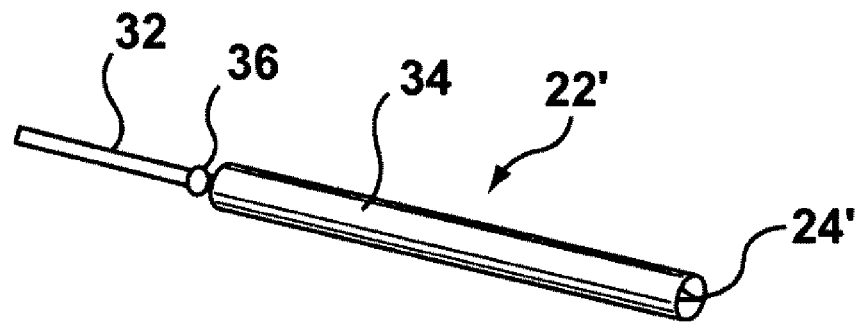
FIG. 2a is an illustration of an RF coil applicator of the RF tissue ablation apparatus of FIGS. 1a and 1b in a non-deployed state.
Figure 2B:
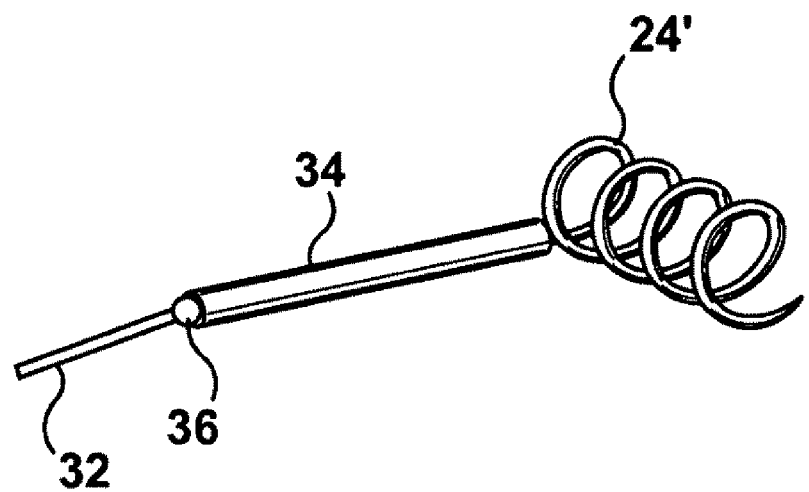
FIG. 2b is an illustration of an RF coil applicator of the RF tissue ablation apparatus of FIGS. 1a and 1b in a deployed state.

Referring now to FIG. 2a, shown therein is an illustration of one exemplary implementation of the RF coil applicator 22' in a non-deployed state. The RF coil applicator 22' includes a cannulating delivery needle 34 with a lumen that houses the RF coil electrode 24 (in a non-deployed state), and a deployment mechanism 26 (not shown) for percutaneous insertion of the RF coil electrode 24'. An electrical connection 36 is also made between the cable 32 and the RF coil electrode 24'; this can be implemented by complimentary electrical connectors on the cable 32 and the RF applicator 22'. The needle 34 is inserted through the skin of the patient into the target site (i.e. the tumor tissue). Once the needle 34 is inserted at the proper location, which can be determined under image guidance using an appropriate imaging technique, the deployment mechanism 26 is actuated and the RF coil electrode 24' emerges from the needle 34, as shown in FIG. 2b (a monopolar RF coil electrode configuration is shown), for insertion into the tumor tissue. In the cannulating needle 34, the RF coil electrode 24' is mechanically deformed, producing stress-induced Martensite. The deployment of the RF coil electrode 24' from the delivery needle 34 results in the removal of the stress allowing the RF coil electrode 24' to reform into its 'trained' coil shape or pre-stressed state.

The deployment mechanism 26 can be configured to deploy the RF electrode coil 24' in a "push and corkscrew" fashion. The deployment mechanism 26 can be located at the distal end of the delivery needle 34. The deployment mechanism 26 can deploy the RF coil electrode 24' such that the coil axis is perpendicular to the direction of insertion of the needle 34. Alternatively, the deployment mechanism 26 can deploy the RF coil electrode 24' such that the coil axis is parallel or oriented in another fashion with respect to the direction of insertion of the needle 34.

There can be other means that are used to apply the RF coil electrode 24 to the tissue target region. Accordingly, use of an applicator with a deployment mechanism is not necessary in all cases. As mentioned, there can be some situations in which the coil electrode 24 can be directly applied to the target tissue region, and a deployment mechanism, and even a structural housing, is not needed.

Figure 3A:
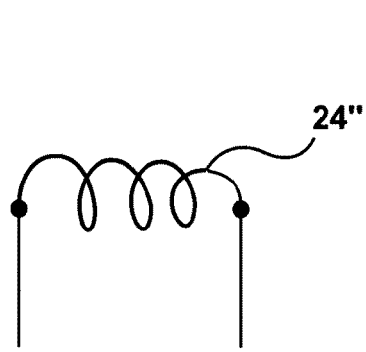
FIG. 3a is an illustration of a bipolar configuration of the RF coil applicator of the tissue ablation apparatus of FIGS. 1a and 1b.
Figure 3B:
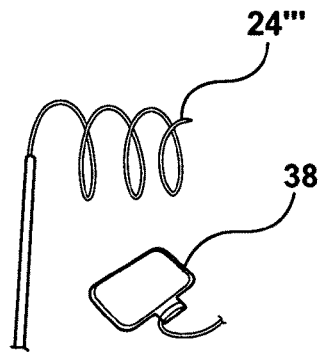
FIG. 3b is an illustration of a monopolar configuration of the RF coil applicator of the tissue ablation apparatus of FIGS. 1a and 1b.

The RF coil applicator 22 can have a bipolar or monopolar coil configuration for the RF electrode coil 24. Referring now to FIGS. 3a and 3b, shown therein are schematic illustrations of a bipolar and monopolar configuration, respectively. For the bipolar configuration, electrical connections are made at each end of the RF electrode coil 24". For use of a bipolar coil in a patient, a monopolar coil can be deployed via a percutaneous insertion through a cannulating delivery needle. The unconnected end of the coil can have a male type connector. A ground lead, with a female connection, can then be inserted and connected to the male end of the coil, via a second insertion point though the skin. In this case, there can be end effects and a flaring out of the generated electric field at the ends of the electrode coil 24" to complete the current paths. The result can be a large current density at the ends of the electrode coil 24" and the heating pattern for the coil 24" starts at the ends of the coil 24". In the bipolar configuration, as will be shown further below, end effects are produced due to a flaring out of the electric field to complete the current paths at the ends of the coil 24". Accordingly, a large current density occurs at the ends of the coil 24" and the heating pattern starts at these areas to produce a significant temperature that can be used to heat tissue. The generated heat then spreads to other regions of the coil 24", as well as the region surrounded by the coil 24".

In the monopolar coil configuration, a connection is made at one end of the RF coil electrode 24'" (i.e. the "active end"), and an additional ground electrode 38 is required to complete the current paths. The end of the RF coil electrode 24'" that does not have a direct physical connection is referred to as the "open end". This configuration most easily allows for the minimally invasive percutaneous insertion of an RF coil electrode through a single cannulating delivery needle.

The ground electrode 38 can be implemented via a ground pad (i.e. ground electrode) (as shown in FIG. 3b) that is placed on the body of the patient. The plane of the ground electrode (i.e. the plane of the ground pad in the case of FIG. 3b) can be oriented perpendicularly or in parallel with respect to the longitudinal axis of the RF coil electrode 24'". Alternatively, any orientation can be used for the ground electrode, although the perpendicular orientation is preferable. In addition, in other embodiments, more than one ground pad can be used.

At the open end of the RF coil electrode 24'", the ground electrode 38 acts as a dispersive electrode and pulls the electric field lines away from the RF coil electrode 24'" so that the distribution of the electric field lines is slightly different than that for the bipolar configuration. However, the geometry of the RF coil electrode 24'" can be adjusted so that the RF coil electrode 24'" can still provide a therapeutic effect. A variety of different configurations of the ground electrode 38 relative to coil axis of the RF coil electrode 24'", and different coil geometries can also be used to adjust the uniformity of the SAR profiles inside the monopolar RF coil electrode 24'". For instance, the coil electrode can be tapered. In addition, the spacing between the coil electrode and the ground electrode can be increased, as is discussed in further detail below.

Figure 4:
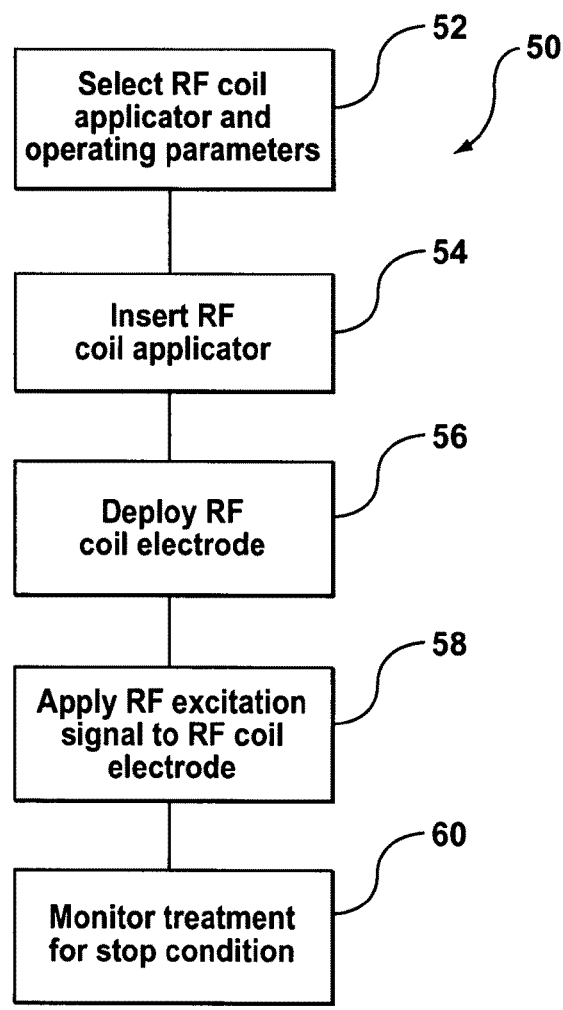
FIG. 4 is a flow chart diagram of an exemplary embodiment of a method for employing the RF tissue ablation apparatus.

Referring now to FIG. 4, shown therein is a flow chart diagram of an exemplary embodiment of a method 50 for employing the RF tissue ablation apparatus 10. At step 52, the parameters of the apparatus 10 are selected based on the type and size of the tumor that needs to be heated/coagulated. The parameters include selecting a particular RF coil applicator 22 (i.e. size, shape and electrode configuration for the RF coil electrode 24), an operating frequency, the amount of power of the excitation current that will be applied to the RF coil electrode 24, and the length of time that the tumor will be exposed to the RF energy provided by the RF coil applicator 22.

At step 54, the RF coil applicator 22 is inserted into the patient so that the RF coil electrode can contact the tumor. Image guidance can be used in this step. Once the RF coil electrode 24' is inserted into the target location, the cable 32 can be connected to the impedance matching circuit 20. At step 56, the RF coil electrode 24' is deployed and if the monopolar configuration is used, then a ground electrode is located on an appropriate location of the patient and connected to the signal generator 16. This step can be optional depending on the type of configuration of the RF coil electrode and the type of RF coil applicator used.

At step 58, the excitation signal is applied to the RF coil electrode with the appropriate amount of power. Based on the geometry of the RF coil electrode 24, and the operating frequency used, power can be applied continuously for the amount of time required to heat the target tissue. For instance, the target tissue can be heated for about 5-30 minutes using continuous power. The amount of heating can also be determined by interstitial tissue temperatures measured in real-time during application of the RF energy. Either of these conditions can be referred to as a stop condition, which is monitored at step 60 to end treatment when the stop condition holds true (i.e. a specified amount of time has elapsed, a specified interstitial temperature has been reached, a specified interstitial temperature has been measured for a certain amount of time, etc.). However, step 60 is optional, as the electrode 24 can simply be applied to the target tissue to provide heat as needed.

It should be noted that the application of continuous power at step 58 is possible based on the geometry of the RF coil electrode 24 and the operating frequency that is used. With conventional RF ablation technology, electric fields exist mainly at the wire of the electrode, due to the geometry and operating frequencies that are conventionally used. Thermal conduction is relied upon to transfer the generated heat throughout the tumor tissue volume. Accordingly, it takes longer to heat the entire tumor tissue, and the temperature at certain areas of the tissue directly adjacent the wire of the electrode increase in temperature quite a bit which causes the impedance of this tissue area to increase. The increase in tissue impedance reduces the effectiveness of the conventional RF electrode to heat the tumor tissue. As a result, power to the conventional RF electrode must be removed, or ramped down, or saline must be inserted at the site, so that the temperature of the heated tissue can decrease, and then the procedure can be applied once more. Accordingly, with conventional RF electrodes, a "start-and-stop" procedure must be used.

In contrast, the geometry of the RF coil electrode 24 and the operating frequencies that are used as described herein also produces an axial electric field within the RF coil electrode 24, i.e. within the volume that is surrounded by the wires of the RF coil electrode 24, that more effectively and efficiently heats the tumor tissue located within this volume. Accordingly, the RF energy produced by the RF coil electrode 24 better targets the entire tumor tissue by directly applying generated heat rather than relying on solely on thermal conduction to heat the tumor tissue. Accordingly, there are no pronounced increases in temperature, and hence increase in tissue impedance, that require the power to the RF coil electrode 24 to be removed. Consequently, RF power can be continuously applied to the tumor tissue with the RF coil electrode until the tumor tissue is fully treated, and the "start-stop" procedure described above for conventional RF coil electrodes does not have to be used.

In addition, the application of heat to a tissue target region must contend with the amount of perfusion (i.e. blood flow) in or near the tissue target region. Perfusion acts as a heat sink, and thus makes it more difficult to apply heat to the target region. With conventional electrodes that are operated at much lower frequencies on the order of hundreds of kHz, the generated electric field is confined to the wire of the electrodes and thermal conduction is relied upon to heat the target tissue. However, in this case perfusion will shunt the generated heat and reduce the effectiveness of the conventional electrodes. In contrast, with the coil electrodes and method of operation described herein, the heat is also generated within the area surrounded by the coil electrode so that the tissue in this area is directly heated and the heat sink effect of perfusion reduced (i.e. the electric field is generated in more locations to more effectively heat the target tissue).

Figure 5:
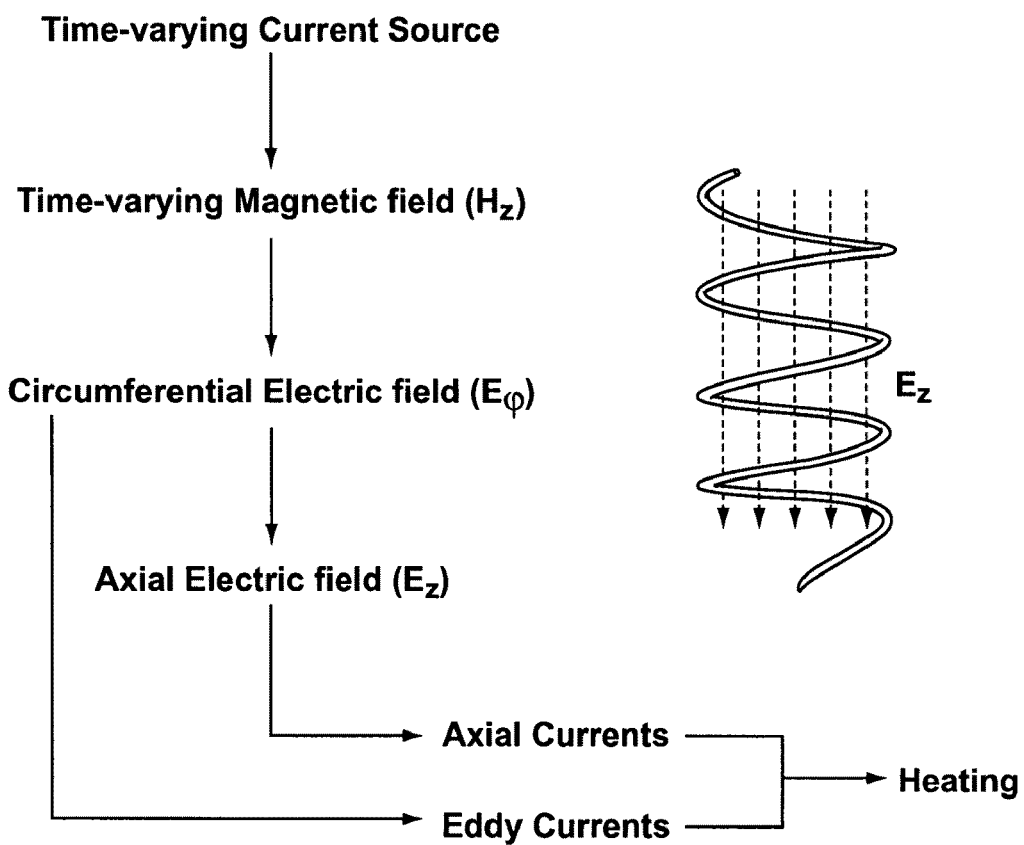
FIG. 5 is an illustration explaining the generation of electric fields that produce heat when the various RF coil electrodes described herein are provided with a time-varying current having a frequency within a certain RF range.

To determine operating parameters and coil geometries that can be used to achieve optimal tumor treatment, the RF coil electrode 24 can be considered to be similar to an infinitely long, tightly wound solenoid. A qualitative approach can be used to describe the fields for an infinitely long solenoid, assuming a current path length much less than the wavelength. The approach is described in FIG. 5. When a time-varying current follows multiple helical loops of a coil, a time-varying magnetic field that is predominantly axial ($H_z$) and azimuthally symmetric is produced inside the coil. According to Faraday's induction law, a time varying axially directed magnetic field produces an electric field that is circumferential ($E_\phi$). The induced electric field gives rise to eddy currents inside the coil. Where this circumferential electric field coincides with the inside of the conductor forming the coil, a redistribution of charge occurs on the conductor surface to yield a tangential electric field ($E_t$) component equal to zero. The redistribution of charge is such that the negative charge is concentrated towards one end of the coil with a corresponding positive charge concentrated towards the opposite end. This separation of charge yields a secondary electric field ($E_z$) that is predominantly axial in the interior region of a long solenoid. To produce these electric fields the operating frequency must be carefully selected. While the frequency must be sufficient for magnetic induction, preferably it should be low enough to: 1) ensure a uniform current along the length of the conductor forming the coil, which is necessary for uniform axial magnetic and electric fields along the coil length (Guerquin-Kern et a/1988), and 2) ensure displacement currents are negligible compared to the coil current to limit the opposing induction field that is set up by the induced eddy currents (Brezovich and Young 1983, Chute and Vermeulen 1981). The axial and eddy currents produced by the axial and circumferential electric fields respectively generate heat for heating the tissue.

Figure 6:
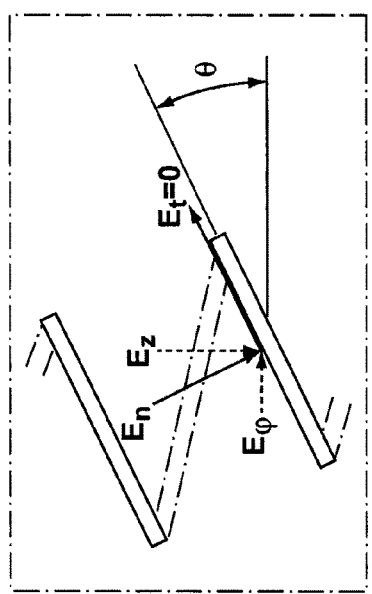
FIG. 6 is a schematic diagram of a perfectly conducting helical coil segment with a finite pitch angle $\theta$.

To clarify the relationship between the electric fields within the coil, FIG. 6 shows a schematic of a perfectly conducting helical coil segment with a finite pitch angle (θ). To satisfy $E_t=0$, the resultant electric field inside the coil must be perpendicular to the conductor surface. This normal component can be decomposed into components along the circumferential (ψ) and axial (z) directions. The surface charge must be distributed such that an axial electric field is produced of sufficient magnitude to ensure that the sum of $E_z$ and $E_\phi$ has a zero component parallel to the wire (see equation 1). As the pitch angle (θ) decreases, the $E_\phi$ component decreases and the $E_z$ component increases. As θ approaches zero, the coil resembles a conducting cylinder and $E_z \gg E_\psi$. In the case of a real conductor with a finite conductivity, the field will penetrate slightly into the conductor the extent of which can be calculated using the skin depth formula given in equation 2, yielding a tangential component that is non-zero but still very small in relation to the normal component. As frequency and/or conductivity increase, the skin depth decreases as does the tangential component.

$$E_\phi \cos \theta + E_z \sin \theta = E_t = 0 \quad (1)$$

$$\text{skindepth} = \sqrt{\frac{2}{\omega \mu \sigma}} \quad (2)$$

In equation 2, the parameter μ is magnetic permeability (i.e. $\mu_o \mu_r$) and the parameter σ is electrical conductivity (S/m). Axial currents are produced in response to this axially directed time-varying electric field, which combined with the eddy currents can be used to heat the tissue throughout the coil interior.

Based on the theory of the ideal solenoid, it is possible that similar electric fields can exist in a loosely wound coil geometry, which can be used for uniform interstitial tissue heating over a large volume. However, factors such as coil length, pitch and local field effects around the coil may influence the electric fields inside the coil. To determine whether such a coil can be useful for heating tumors, experimental models and three-dimensional finite element analysis can be used to model the electric fields of this short, loosely wound coil geometry of finite wire size. Analytical models are not sufficient to describe the electric fields of this coil because the models assume an infinitely long, tightly wound solenoid and a conducting wire of negligible cross section.

To determine the performance of the coil electrode, experimental models were used to confirm the existence of electric fields throughout the coil interior, including the coil center. A test coil electrode made from Nitinol (as described above) having a 2 cm diameter, a 1 cm pitch, and a 4.5 cm length was cast in a gel phantom made of acrylamide (Unsion BioTek, Hamilton, ON, Canada) and bovine serum albumin (Boval Company Ltd., Cleburne, Tex., USA). This phantom was based on an ultrasound phantom recipe developed by McDonald (2004) for testing interstitial ultrasound transducers for thermal therapy. In the phantom, the Intralipid component (required to mimic the ultrasound scattering properties of tissue) was replaced with an equivalent volume of deionized water. The phantom is transparent, which permits the placement of temperature probes at known locations inside the phantom. Also, the phantom coagulates between 45-50° C. when heated. The test coil was driven at frequencies of 460 kHz, 5 MHz, 27.12 MHz and 75 MHz using a 3325A Synthesizer/Function Generator (Hewlett-Packard, Loveland, Colo.) and an A-300 RF Power Amplifier (ENI, Rochester, N.Y.) via flexible, unbalanced coaxial cables attached to both ends of the coil (i.e. a bipolar configuration), and an impedance matching circuit for maximum power delivery to the test coil. The coil electrode was operated at the RF frequencies of 460 kHz, 5 MHz, 27.12 MHz and 75 MHz to demonstrate the frequency dependence of the electric fields inside the test coil and to determine the optimal frequency of operation.

Numerical models were used to calculate the electric fields and SAR patterns at frequencies that could not be investigated experimentally and to provide electric field distributions and SAR profiles along the length of the coil, which could not be extrapolated from the limited number of measured data points.

The coil was supplied with a net input power of approximately 100 Watts measured by a directional wattmeter (DAIWA Industry Company, Ltd., Japan). The SAR (specific absorption rate), which is proportional to the electric field intensity (see equation 3, Ryan et al 1990), was measured at each frequency. An E-field probe was not used for direct measurement of electric field strength because it can perturb the applicator field pattern, compromising the accuracy of the results (see equation 4, Iskander and Tumeh 1989). As an alternative, and assuming that only heat generation occurs (i.e.: no heat flow), SAR can be linearly related to temperature rise in the medium over a short time period (seconds) (Ryan et al 1990).

$$SAR = \frac{\sigma}{2}|E|^2 \quad (3)$$

$$SAR = \rho c \frac{\Delta T}{\Delta t} \quad (4)$$

The parameter E is the magnitude of the electric field (V/m), $\rho$ is the density of the medium (kg/m$^3$), c is the specific heat (J/kgK), and $\Delta T$ is the temperature rise over time $\Delta t$.

Figure 7:
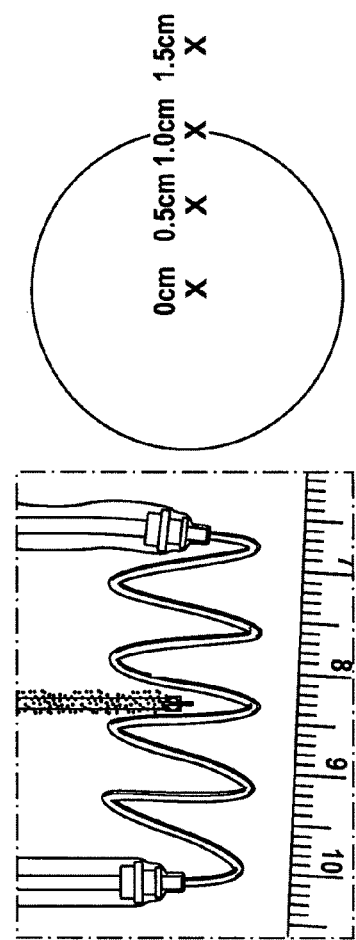
FIG. 7 is an illustration showing a test coil cast in a polyacrylamide bovine serum albumin phantom with coaxial cables connected at both ends of the test coil and temperature probes inserted at the test coil mid-plane, at selected radial positions from the coil center.

Temperature rise was measured at 4 point locations inside the phantom using four Fluoroptic temperature probes (Model 3100SMM, Luxtron, Santa Clara, Calif., USA) located at selected radial positions at the coil mid-plane, perpendicular to the coil axis. FIG. 7 shows the test coil electrode with the temperature probes and the radial positions used for temperature measurement. Measurements at the coil mid-plane should not be affected by fringe field effects, which occur near the ends of a coil (Lorrain and Corson 1962, Ryff 1972). Temperature measurements were recorded after 5 seconds of heating to minimize errors arising from thermal diffusion. For each frequency and at each radial position, an average SAR was calculated from 3-5 temperature measurements and normalized to the maximum SAR. To complement the SAR data, photographic images of the coagulation patterns were captured after 3 minutes of heating.

Figure 8:
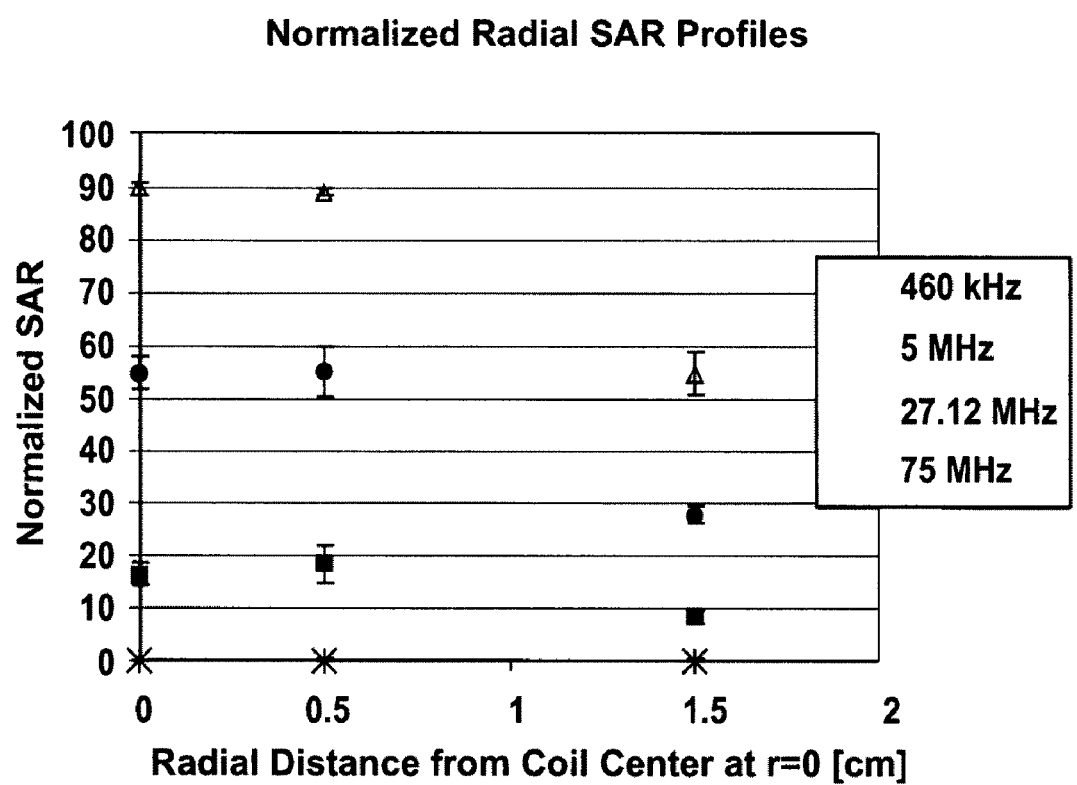
FIG. 8 is a plot showing the frequency dependence of measured radial SAR Profiles at the test coil mid-plane, at selected radial distances from the test coil center (r=0 cm), normalized to the maximum SAR measured for that particular experiment.

Results of the phantom heating experiments are shown in FIG. 8. The results show the SAR values measured at the test coil mid-plane at different distances from the test coil center, for each test frequency. As the test frequency increased, the uniformity of the radial SAR profiles improved. At 460 kHz, there was no measurable SAR in the coil center (r=0 cm) whereas at frequencies of 5 MHz, 27.12 MHz and 75 MHz, there was a measurable SAR at r=0 cm. As frequency increased, the ratio of the SAR at the coil center (r=0 cm) to the SAR at the wire conductor (r=1 cm) increased. The ratio of SAR measured at 1.5 cm (0.5 cm from the wire) to the SAR at the wire also increased with frequency.

Figure 9:
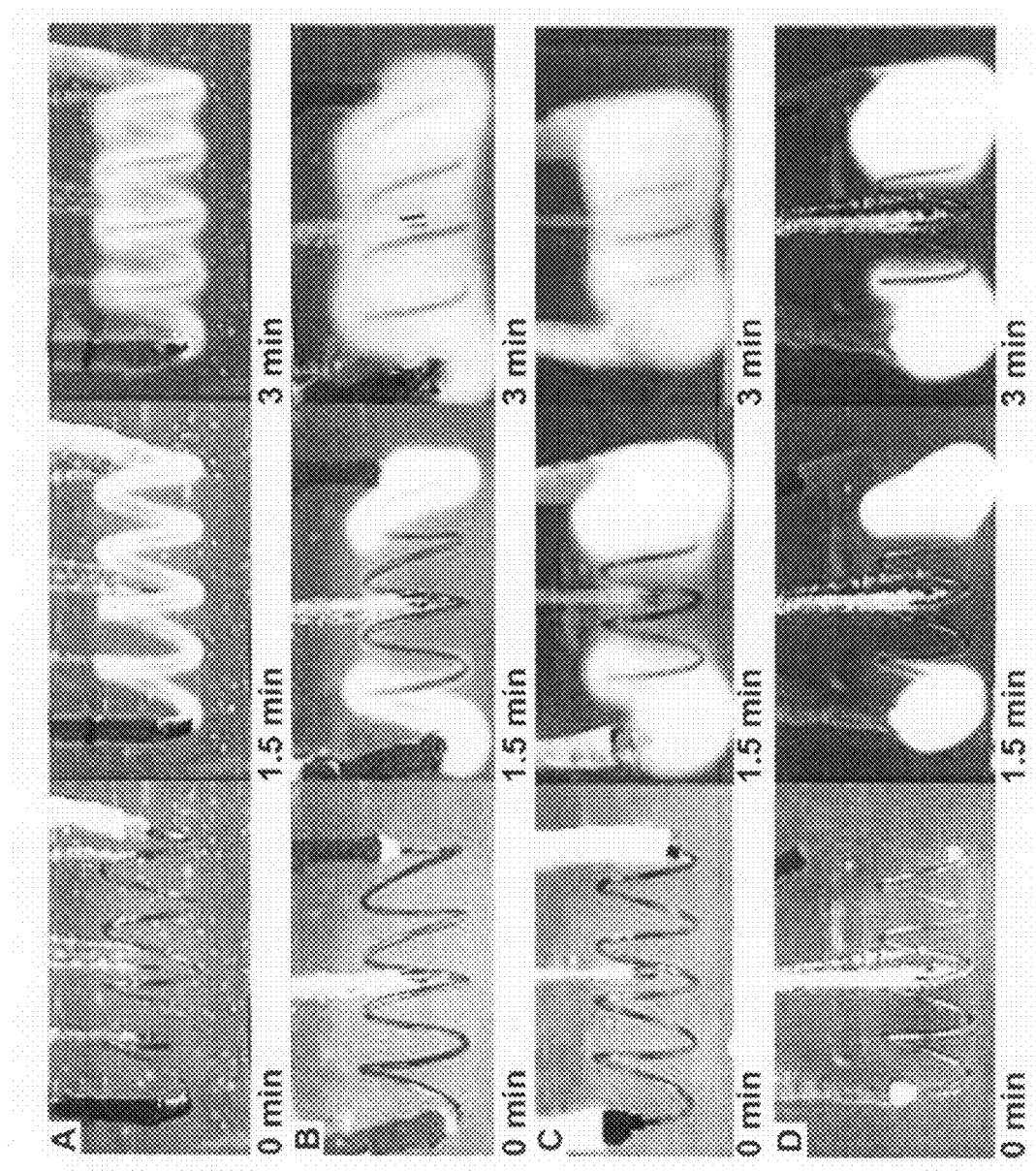
FIG. 9 shows the time dependence and frequency dependence of coagulation patterns produced by the test coil in the phantoms during a 3-minute heating period.

FIG. 9 shows photographic images of the coagulation patterns in the phantom produced during a 3 minute heating period that show the volumetric power deposition patterns at each test frequency (power deposition is proportional to electric field intensity). Images were acquired at 0 minutes, 1.5 minutes and 3 minutes at A) 460 kHz, B) 5 MHz, C) 27.12 MHz and D) 75 MHz. The white regions in the images indicate coagulation of the bovine serum albumin in the phantom, which occurs when the phantom has reached a temperature of 45° C.-50° C. The phantom temperature before heating was approximately 20° C. At 460 kHz, coagulation was confined to the region immediately surrounding the conducting winding. This result was consistent with the measured SAR at 460 kHz, which was non-zero at the wire and zero everywhere else. At 5 MHz and 27.12 MHz coagulation began at the outer turns of the coil (termed end effects) and proceeded to develop from inside the coil, indicating that the SAR at the ends of the coil was higher than at the coil mid-plane. At 75 MHz, a similar result was observed, except that after 3 minutes of heating, coagulation had not yet developed in the middle of the test coil.

The numerical models were examined using FEMLAB® 3.1 (Comsol, Burlington, Mass., USA), which is a finite element software package that was used to calculate the electric and magnetic fields of a loosely wound coil. For problems in electromagnetics, FEMLAB® uses vector elements because they ensure continuity of the tangential component of the electric and magnetic fields and better fulfill the divergence free conditions than scalar elements (Kumaradas and Sherar 2002).

Calculated SAR values based on the numerical model were compared to measured values in order to validate the numerical model. For the measurements, a test coil with a 2 cm diameter, a 1 cm pitch, and a 4.5 cm length operated at 27.12 MHz was cast in a polyacrylamide/bovine serum albumin phantom. Temperatures were measured at 4 radial positions from the coil center at the coil mid-plane following 5 seconds of heating and 100 Watts of power applied to the test coil. From equation 3, absolute SAR was calculated using the measured temperature rise, a measured phantom density (1050 kg/m$^3$) and a specific heat equal to water 4180 J/kgK (the phantom is 80% water). To ensure an accurate source input for the model, the peak-to-peak voltage applied across the phantom-loaded test coil was measured using an oscilloscope (PM3323, Philips, The Netherlands) and a high impedance probe (10 M$\Omega$ PM8929/39, Philips, The Netherlands). The dielectric properties of the phantom were also measured for input into the numerical model. Using a custom-made coaxial sensor (Stuchly and Stuchly 1980, 1982) and a vector voltmeter (HP 8508A, Houston, Tex., USA), the dielectric properties of the phantom were calculated from the reflection coefficient measured at the probe/sample interface (Chin and Sherar 2001).

A cubic domain (12 cm×12 cm×12 cm) and coil geometry representative of the real phantom and test coil were drawn in FEMLAB®. The measured electrical properties of the Nitinol wire (resistivity=82 m$\Omega$·cm or $\sigma$=1.2195e6 S/m; http://www.nitinol.info/pdf_files/se508_wire_data.pdf) and phantom sub-domain ($\sigma$=1.1 S/m, $\epsilon_r$=80) were entered into the calculation, as was the operating frequency (27.12 MHz). Continuity of the normal component of the electric current was specified at the coil boundaries. At the outer boundaries of the phantom domain, the electric displacement D was set to zero outside the boundary, corresponding to electrical insulation. A voltage was applied at both end faces of the coil corresponding to the measured positive and negative peak voltages (±V/2). FEMLAB® was used to mesh the coil and phantom domains generating 49,138 elements and 74,727 degrees of freedom. This mesh density was achieved by iteratively increasing the mesh density until a negligible change (<5%) in the SAR value was achieved while still maintaining a practical computation time (2 hours). A time-harmonic analysis was applied to Maxwell's equations from which the electric and magnetic vector potentials were solved. The calculation required both scalar and vector elements, increasing the complexity and size of the solution. From the simulation results, the SAR values at the test coil mid-plane at radial positions of 0 cm, 0.5 cm, 1.0 cm and 1.5 cm were extracted and compared to measured results.

Figure 10:
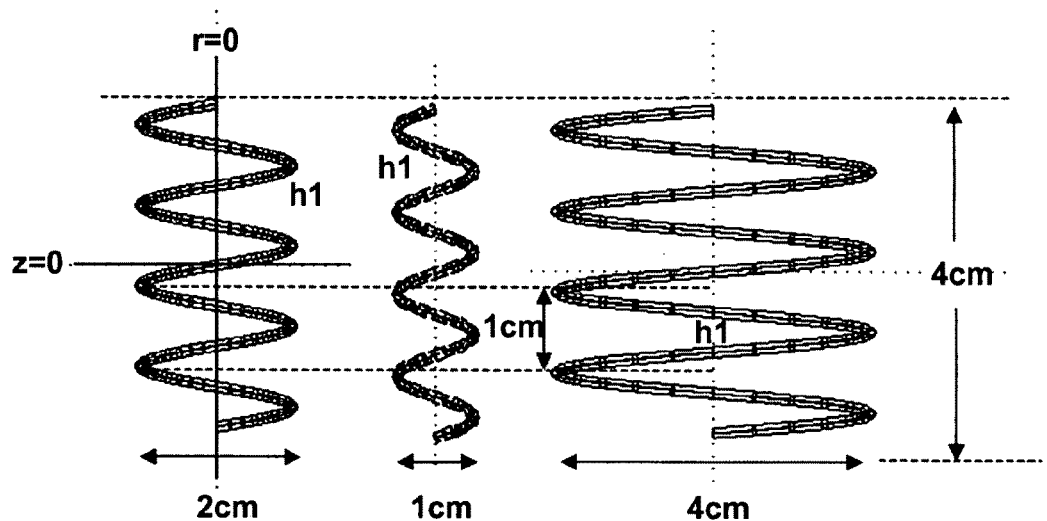
FIG. 10 is an illustration of test coil geometries having different aspect ratios.

Using the procedure described for numerical model validation, the SAR profiles of a test coil operated at frequencies of 27.12 MHz, 75 MHz and 150 MHz were examined and compared using FEMLAB®. The SAR profiles of other test coils, each having a length of 4 cm and a 1 cm pitch but with diameters of 2 cm, 1 cm and 4 cm respectively (see FIG. 10), for an excitation current at 27.12 MHz, were also calculated to determine the effect of varying the Aspect Ratio (AR) of the test coil. In order to determine the effect of frequency and geometry on SAR patterns, axial and radial SAR profiles were plotted along coordinates shown in FIG. 10. Radial profiles were plotted at the coil mid-plane (at z=0 cm) perpendicular to the coil axis at radial positions from the coil center (at r=0 cm), shown on the leftmost test coil in FIG. 10. Axial profiles were plotted on-axis (r=0 cm), also shown on the leftmost test coil in FIG. 10. Each profile was normalized to the maximum SAR value along its profile for each simulation.

The electromagnetics model was validated by comparing measured and calculated absolute SAR values at selected radial positions of 0 cm, 0.5 cm, 1.0 cm and 1.5 cm located at the coil mid-plane, for a 2 cm diameter test coil with a 1 cm pitch, and 4.5 cm length operated at 27.12 MHz. The results are shown in Table 1, which shows an excellent agreement between measured and calculated results.

TABLE 1

Comparison of measured and calculated absolute SAR values.

| SAR ($W/cm^3$) | At r = 0 cm | At r = 0.5 cm | At r = 1.0 cm | At r = 1.5 cm |
|---|---|---|---|---|
| Experimental | 0.78 $W/cm^3$ | 0.8 $W/cm^3$ | 1.5 $W/cm^3$ | 0.38 $W/cm^3$ |
| Theoretical | 0.75 $W/cm^3$ | 0.76 $W/cm^3$ | 1.4 $W/cm^3$ | 0.36 $W/cm^3$ |

Figure 11:
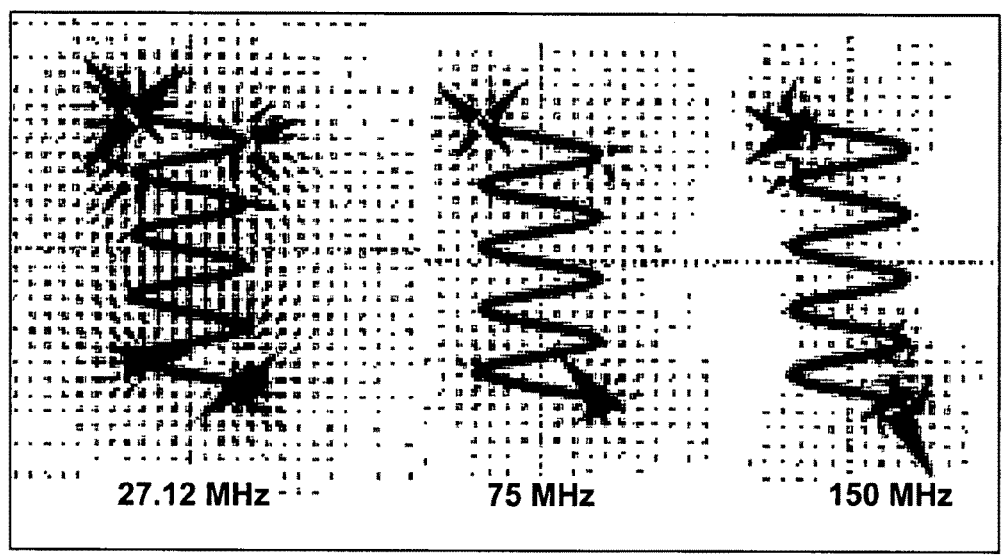
FIG. 11 is an illustration of simulation results of the electric field vector distributions on a two-dimensional plane through the coil center of a test coil at various frequencies.
Figure 12:
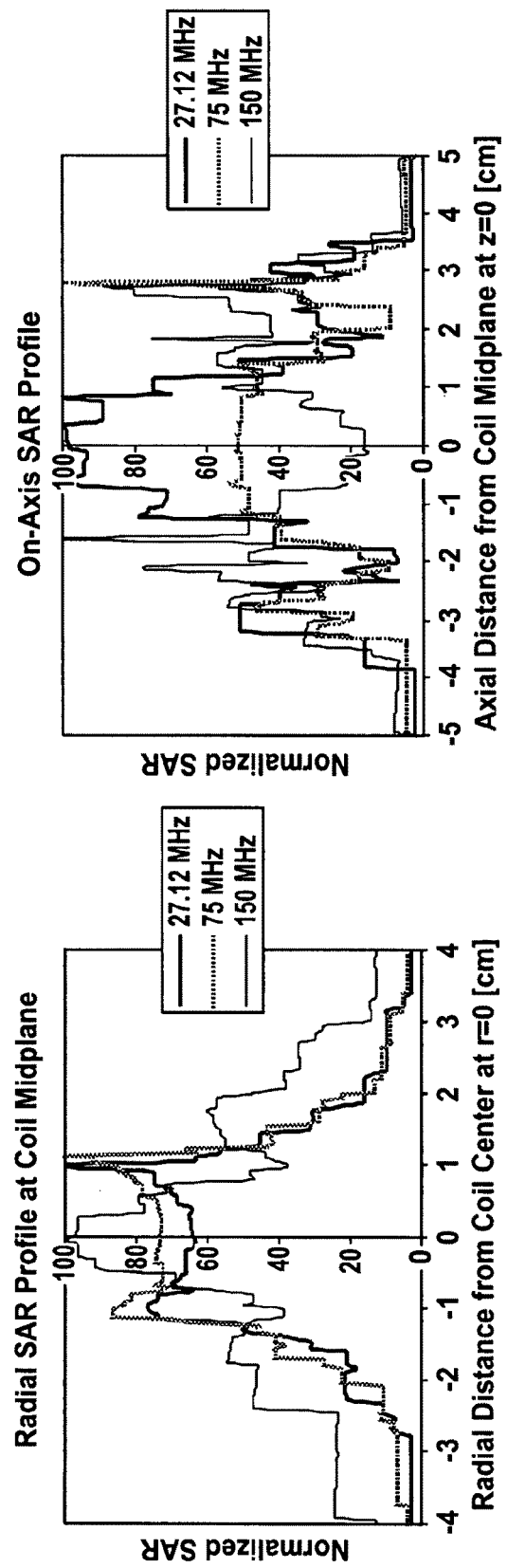
FIG. 12 includes two plots showing the frequency dependence of calculated radial SAR profiles (left) and calculated axial SAR profiles (right)

FIG. 11 shows FEMLAB® simulation results of the electric field vector distributions on a two-dimensional plane through the coil center (r=0 cm) for a 2 cm diameter, 1 cm pitch and 4.5 cm length loosely wound test coil operated at 27.12 MHz, 75 MHz and 150 MHz, respectively. The results were plotted with the same number and size of vector points. Electric field intensity is proportional to cone size. At 27.12 MHz, the size and pattern of the axially-directed vectors is homogeneous in the center of the test coil, neglecting the regions at the end turns. At 75 MHz and 150 MHz, the homogeneity of the axially-directed vector distribution inside the test coil decreases. FIG. 12 shows the radial SAR profile of the 2 cm diameter coil plotted at the coil mid-plane, with the coil center at 0 cm. The coil mid-plane is at z=0 cm and the ends of the coil are located at ±2.25 cm. As frequency increases, the ratio of SAR at r=0 cm to the SAR at r=1 cm increased. At 150 MHz, the shape of the SAR profile was different with two side lobes at r>1 cm and r<1 cm. FIG. 12 also shows the on-axis SAR profiles for these simulations. As the operating frequency increases, the ratio of the on-axis SAR at the test coil mid-plane to the on-axis SAR at the test coil ends decreases, i.e.: uniformity of the axial SAR profile deteriorated with increasing frequency. At 150 MHz, the on-axis SAR profile is much more irregular with the maximum SAR on-axis, occurring at the ends of the test coil and decreasing towards the test coil center.

Figure 13:
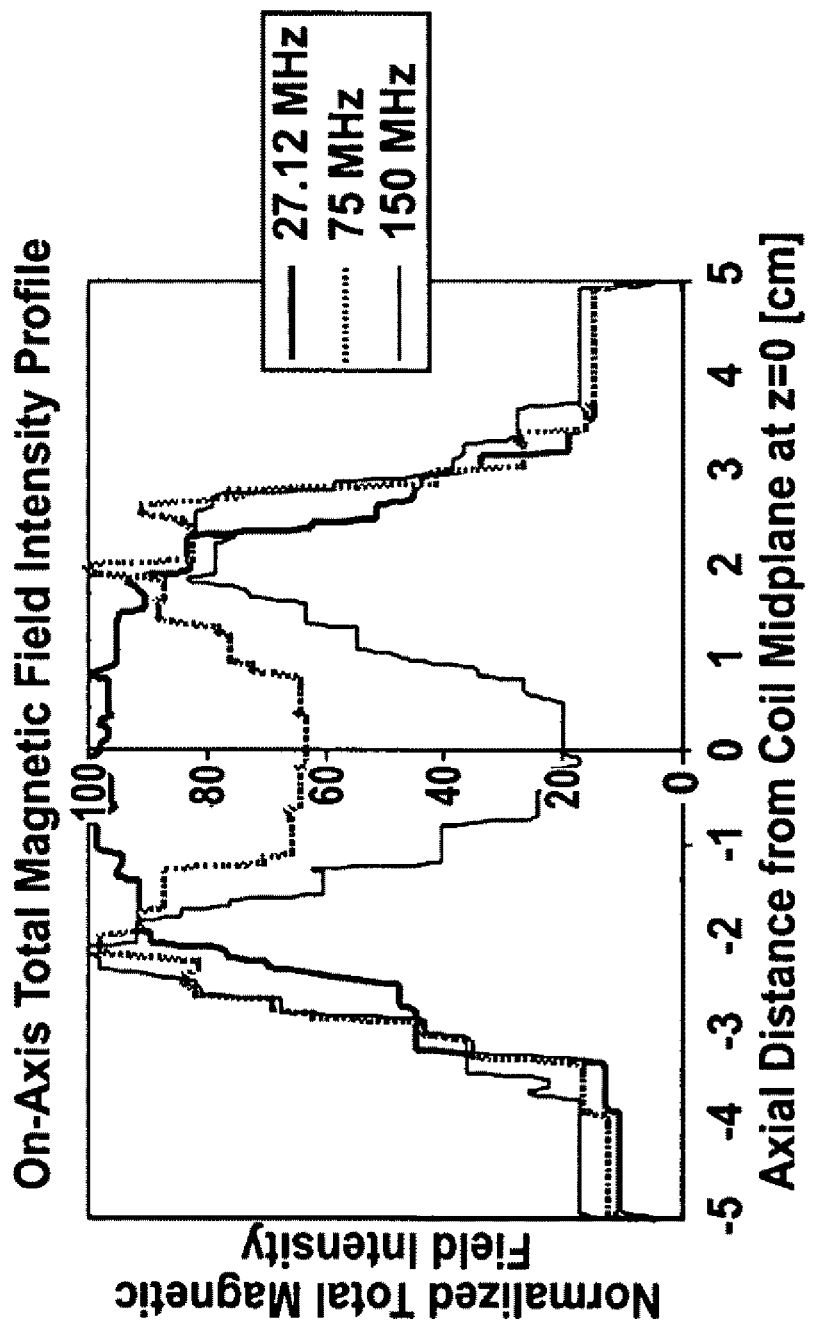
FIG. 13 is a plot showing the frequency dependence of calculated axial total magnetic field intensity profiles for the test coil.

Total magnetic field intensity profiles on-axis have also been plotted. FIG. 13 shows a decrease in the total magnetic field intensity towards the coil center, with increasing frequency. At 27.12 MHz, the total magnetic field intensity is quite uniform along the length of the test coil.

Figure 14:
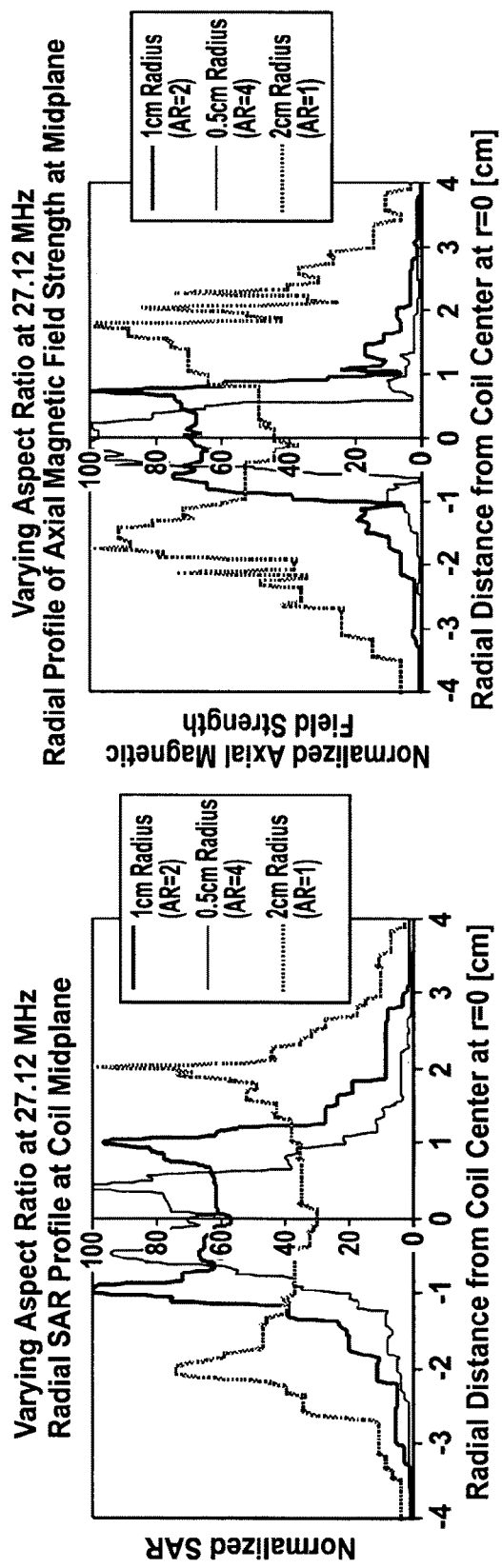
FIG. 14 includes two plots showing the dependence of calculated radial SAR profiles on aspect ratio (left), and the dependence of calculated axially directed magnetic field strength on aspect ratio (right).
Figure 15:
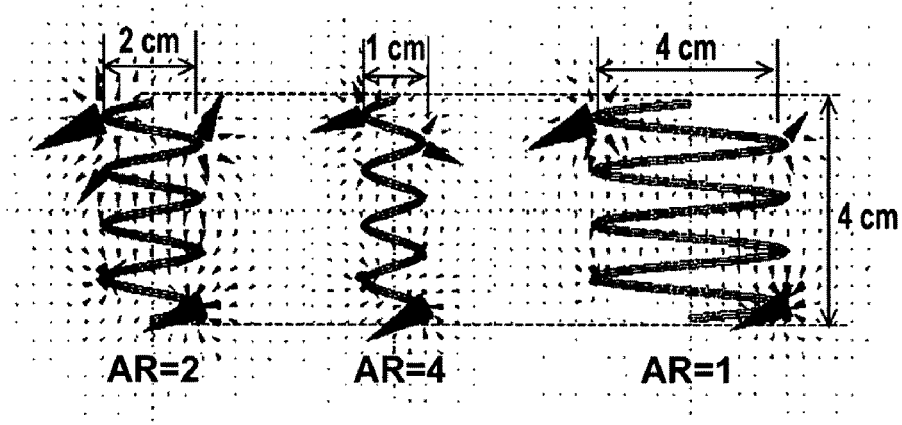
FIG. 15 is an illustration of electric field vector distributions on a two-dimensional plane through the coil center for test coils with aspect ratios (AR) of 2, 4 and 1 and operated at 27.12 MHz.
Figure 16:
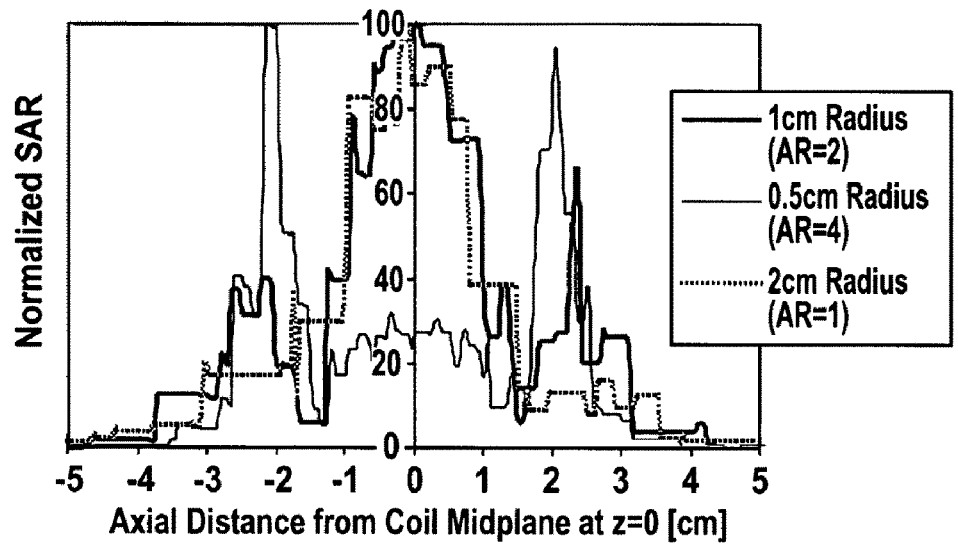
FIG. 16 is a plot showing the dependence of calculated axial SAR profiles on aspect ratio.

FEMLAB® was also used to calculate the electric and magnetic fields of test coils having varying aspect ratios. Radial SAR and magnetic field strength profiles of three coil geometries operated at 27.12 MHz, were calculated and are shown in the left and right plots, respectively, of FIG. 14. Uniformity in the radial SAR profiles improved with increasing aspect ratio. The radial profiles of axially-directed magnetic field strength at the test coil mid-plane show a similar trend, i.e.: uniformity of the axially-directed magnetic field improved with increasing aspect ratio. FIG. 15 shows the electric field vectors on a two-dimensional plane through the center (r=0 cm) of the three test coils operated at 27.12 MHz. The results were plotted with the same number and size of vector points. The electric field intensity is proportional to cone size. The test coil with an aspect ratio of 2 shows the most uniform distribution of axially-directed cone vectors (neglecting end effects) compared to the test coils with aspect ratios of 4 and 1. Axial SAR profiles (FIG. 16) showed no fundamental difference in the shape of the profile inside the test coil.

The experimental and numerical models confirmed the presence of an axially-directed electric field inside the bipolar coil geometry, which can be exploited for producing large, homogeneous coagulation volumes. However, to produce an electric field that is essentially uniform in the interior of the RF coil electrode 24, the coil 24 is operated in a frequency range sufficient for magnetic induction, but low enough to ensure a uniform current along the length of the coil, and displacement currents that are negligible compared to the coil current.

The experimental results showed the uniformity of the radial SAR profile improved with increasing frequency. At 460 kHz, there was no measurable SAR inside the test coil, which suggests negligible coupling between the electric and magnetic fields. Due to the lower resistance of the conducting wire of the test coil at 460 kHz, the test coil acts as a voltage source. The resultant electric field is determined by the voltage distribution which is confined to the conducting wire, i.e.: $E=-\nabla V$. At this frequency, the electric field is dominated by the static charge component, which is importantly very close to the wire (Lorrain and Corson 1962). Accordingly, for conventional RF applicators, the electric fields and subsequent absorbed power pattern is confined to a region immediately surrounding the conducting wire of the electrode. This explains the poorer performance of the conventional RF ablation electrodes, and why heating is localized to the area of the target tissue right at the conducting wire of the conventional RF coil electrodes, which then results in very high temperatures, and high tissue impedances which then requires the "start-and-stop" technique for tissue ablation.

However, as the frequency was increased to between 5 MHz and 75 MHz, an electric field was produced in the center of the test coil. There is sufficient coupling between the electric and magnetic fields at these frequencies to produce magnetically induced electric fields, which are a combination of both static and dynamic charges, i.e.: $E=-\nabla V-\partial a/\partial t$ (Lorrain and Corson 1962). The magnetically induced electric fields includes electric fields within the coil and not simply around the conducting wire as is the case for conventional RF electrodes operated in the 460-500 kHz. Taking this one step further, as the frequency is increased even further, the contribution of the dynamic charge component to the electric field will dominate, $E=-\partial A/\partial t$, which may explain the larger central SAR compared to the SAR at the wire, shown at 150 MHz.

The frequency dependence of the radial SAR profiles can also be explained by considering the local field effects around the conducting wire. The coil can be considered to be a series of current elements joined end-to-end. Examination of the fields around a current element Idl, i.e.: a thin wire segment that is considered so short that the current (I cos ωt) is essentially constant along its length, show electric fields with radiative, inductive and electrostatic terms. Calculation of the electromagnetic field at an arbitrary point P at some distance R from the wire segment yields a circumferential magnetic field ($H_\phi$), a radial electric field component ($E_\rho$), and a polar electric field component ($E_\theta$). According to Jordan and Balmain (1968):

$$E_\theta \alpha \left( \frac{\omega}{\rho}, \frac{1}{\rho^2}, \frac{1}{\omega \rho^3} \right) \quad (5)$$

$$E_\rho \alpha \left( \frac{1}{\rho^2}, \frac{1}{\omega \rho^3} \right)$$

where ρ is the radial distance from the coil center. Both $E_\rho$ and $E_\theta$ have an induction term ($1/\rho^2$) and an electrostatic term ($1/\omega\rho^3$). The induction term contributes to the energy that is stored in the electric field. The electrostatic term arises from the accumulation of charge on the conducting wire and has a form that is similar to the electrostatic field of an infinitesimal electric dipole, which has radial and polar electric field components that also vary as $1/\rho^3$ (Jordan and Balmain 1968). The electrostatic term is inversely proportional to frequency. This was evident in the experiments and simulations, which showed a decrease in the SAR at the conducting wire relative to the central SAR, with increasing frequency. The electric field $E_\theta$ contains an inverse distance term or radiation term ($\omega/\rho$) that arises from the finite time of propagation of electrical signals. This term, which is proportional to frequency, contributes to the flow of energy away from the source and may explain the side lobes observed in the 150 MHz radial SAR profile.

The most uniform radial SAR profiles are produced at frequencies that contribute both static and dynamic charge components to the electric fields. Increasing frequency to bring the ratio of static to dynamic charge closer to one, occurred at the expense of axial uniformity. The uniformity of the calculated axial SAR profiles deteriorated with increasing frequency. The axial profiles calculated at 27.12 MHz and 75 MHz showed two identifiable phenomena: 1) a decrease in the SAR just before the ends of the test coil and 2) a smaller increase in SAR just past the ends of the test coil. The first observation can be explained by the decrease in magnetic induction at the ends of the test coil due to the fact that the magnetic field lines flare out in order to form a closed path (Lorrain and Corson 1962, Ryff 1972). Ryff (1972) refers to this phenomenon as leakage flux. As the field lines flare out, they impinge upon the outer turns of the test coil causing eddy current losses in the conducting wire and significant localized heating. This also explains the second observation, i.e.: the increase in the axial SAR profile just beyond the ends of the test coil, and the nature of the coagulation patterns produced in the phantoms. The eddy current losses in the outer turns of the test coil were larger than the circumferential and axial currents exploited for heating the region inside the test coil, resulting in non-uniform coagulation patterns. As frequency increases, the skin depth in the outer turn of the test coil is reduced, and the induced currents are concentrated in the region closer to the surface, resulting in significantly more power loss and localized heating (Namjoshi and Biringer 1990, 1991). At 150 MHz, the SAR at the test coil mid-plane was much less than the SAR at the test coil ends, on-axis. The reduction in the total on-axis magnetic field strength towards the test coil center suggests that the displacement current density is no longer negligible compared to the coil current. According to Lenz's law, the opposing induction fields set up by the induced eddy currents are sufficient to reduce the applied axial magnetic field (Brezovich and Young 1983, Chute and Vermeulen 1981, Lorrain and Corson 1962).

The effects of coil geometry were evaluated by varying the aspect ratio. The axial magnetic field inside a short solenoid is proportional to the ratio of the coil length to coil radius (Lorrain and Corson 1962 and Knoepfel 2000). As this ratio increased, the magnetic field strength and the magnetically induced electric fields inside the coil also increase, because the electromotive force induced in the solenoid is equal to minus the rate of change of the magnetic flux. Examination of axial SAR profiles of test coils with varying aspect ratios showed increased end effects relative to the central SAR for larger aspect ratios. This can be explained by increased eddy current losses from the outer turns. As the test coil diameter increased, the contribution from the eddy currents to the on-axis SAR at the test coil ends decreased. The effects of varying pitch were also examined (results not shown), and showed that as the number of turns per unit length decreased, the uniformity of both the radial and axial SAR profiles deteriorated. As the pitch is increased, there were not enough conducting turns to adequately form a test coil, and the uniformity of the axial magnetic and electric fields was compromised.

These test results show that a loosely wound interstitial helical coil with dimensions comparable to large tumor sizes (>3 cm), operated at radio frequencies that are higher than those used conventionally (i.e. 460 KHz) can produce coagulative necrosis of a large tumor volume via resistive heating mechanisms set up by the coil's time-varying electric fields. The test results also showed the presence of a reasonably uniform, axially directed electric field inside a coil that is operated at radio frequencies in the low tens of MHz range. Based on the tradeoff between radial and axial uniformity of the SAR profiles, one exemplary embodiment of an RF electrode coil can have a 2 cm diameter coil, a 4 cm length and a pitch of 1 cm and can be operated at 27.12 MHz to produce a uniform coagulation volume.

Tests were also conducted to assess the performance of an RF coil electrode having a monopolar configuration thus requiring an external ground electrode to complete the current path. The external ground plane serves as the dispersive electrode. The monopolar configuration is advantageous for implementing a minimally invasive procedure involving a single needle insertion of the RF electrode applicator.

Figure 17:
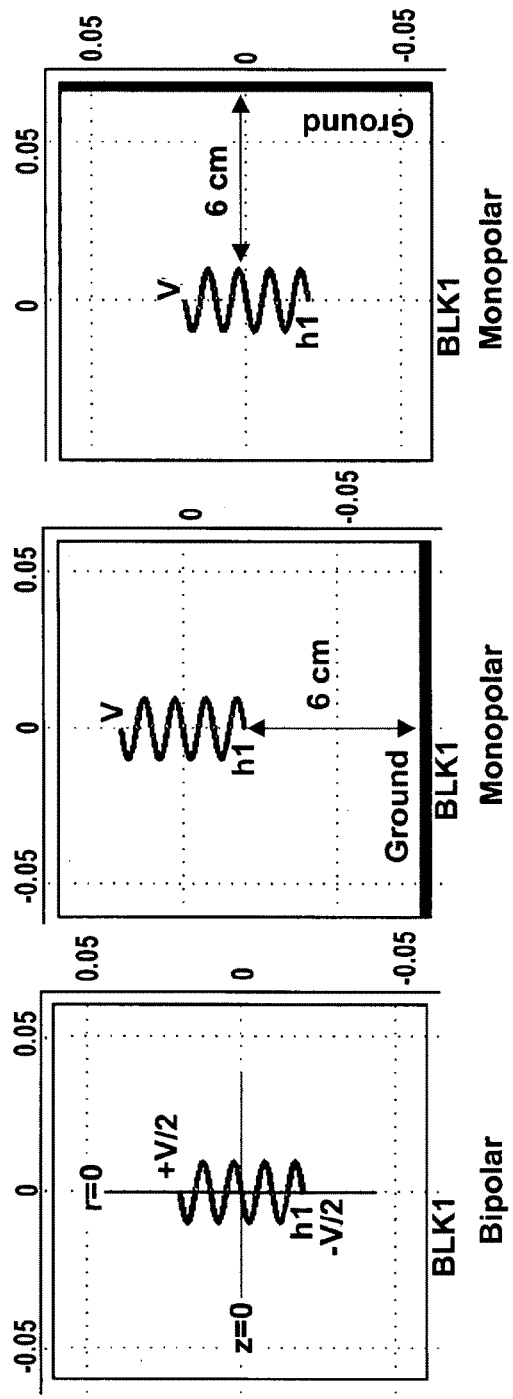
FIG. 17 shows a bipolar test coil (left), and monopolar coils (center and right) with a ground pad perpendicular ($\perp$) to the coil axis, and parallel ($\parallel$) to the coil axis, respectively.

Experiments were conducted to determine the performance of the monopolar electrode configuration with respect to the bipolar electrode configuration, and to determine the extent to which the ground plane perturbs the electric fields inside the coil electrode. FEMLAB® was used, as specified above, to calculate the electric fields and SAR profiles of: 1) a bipolar test coil, 2) a monopolar test coil with a ground plane oriented perpendicular to the coil axis and 3) a monopolar test coil with a ground plane oriented parallel to the coil axis. Each test coil had a diameter of 2 cm, a 1 cm pitch and a 4 cm length. In the latter two cases, the ground electrode (a ground pad was used in the experiments) was located 6 cm from the end or edge of the test coil. This distance of the ground pad was selected to mimic the maximum distance that could be tested experimentally given the size of the phantom mould. FIG. 17 shows a bipolar test coil (left) with a voltage applied at the end faces of the test coil (±V/2), and monopolar coils (center and right) with a ground pad perpendicular (⊥) to the coil axis, and parallel (∥) to the coil axis, respectively. For the monopolar test coils, the voltage was applied at one end face of the test coil (V). Locations of radial and axial profiles are shown on the leftmost coil. Radial profiles were plotted at the coil mid-plane (at z=0 cm), perpendicular to the test coil axis, at radial positions from the test coil center (at r=0 cm). Axial SAR profiles calculated on-axis (r=0 cm) and radial SAR profiles calculated at the coil mid-plane (z=0 cm), perpendicular to the test coil axis, were plotted and compared for the three cases. Each profile was normalized to the maximum SAR value along its profile for each simulation. Electric field vector distributions plotted on a coronal plane through the coil center were also compared.

FEMLAB® 3.1 was used to calculate the electric fields and SAR profiles of the monopolar test coil with a ground plane. A frequency of 27.12 MHz was specified. At the test coil boundaries, continuity of the normal component of the electric current was specified. At the outer boundaries of the phantom domain, the electric displacement D was set to zero outside the boundary, corresponding to electrical insulation, except at the boundary representative of the ground plane which was set to zero potential. A voltage was applied at one end face of the test coil. Electrical continuity was specified at the opposite end face of the test coil. FEMLAB® was used to mesh the test coil and phantom domains generating 49,138 elements and 74,727 degrees of freedom. This mesh density was achieved by iteratively increasing the mesh density until a change in the SAR value of less than 5% was achieved.

To determine the extent to which the ground plane perturbs the electric fields inside the test coil, FEMLAB® was used to calculate the electric fields and SAR profiles of the test coil configurations shown in FIG. 17 in a simulated phantom domain at an operating frequency of 27.12 MHz. Axial SAR profiles calculated on-axis (r=0 cm) and radial SAR profiles calculated at the coil mid-plane (z=0 cm), perpendicular to the coil axis, were plotted and compared for the three cases. Each profile was normalized to the maximum SAR value along its profile for each simulation. Electric field vector distributions plotted on a coronal plane through the coil center were also compared.

Figure 18:
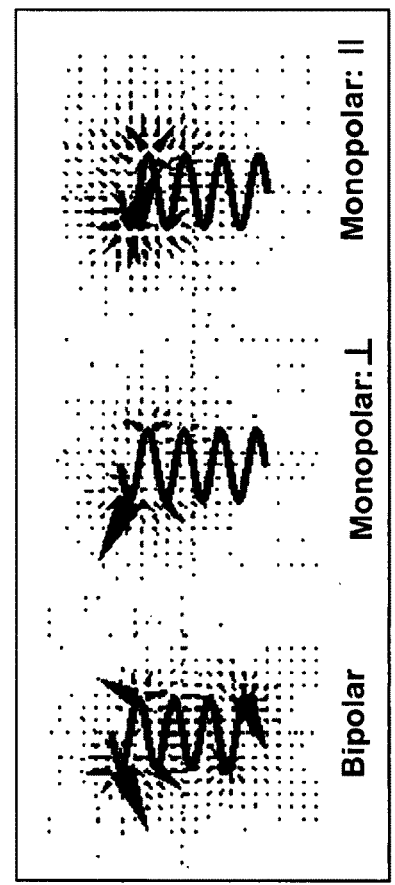
FIG. 18 is an illustration of electric field vector distributions through test coils centers for test coils operated in the configurations shown in FIG. 17.
Figure 19:
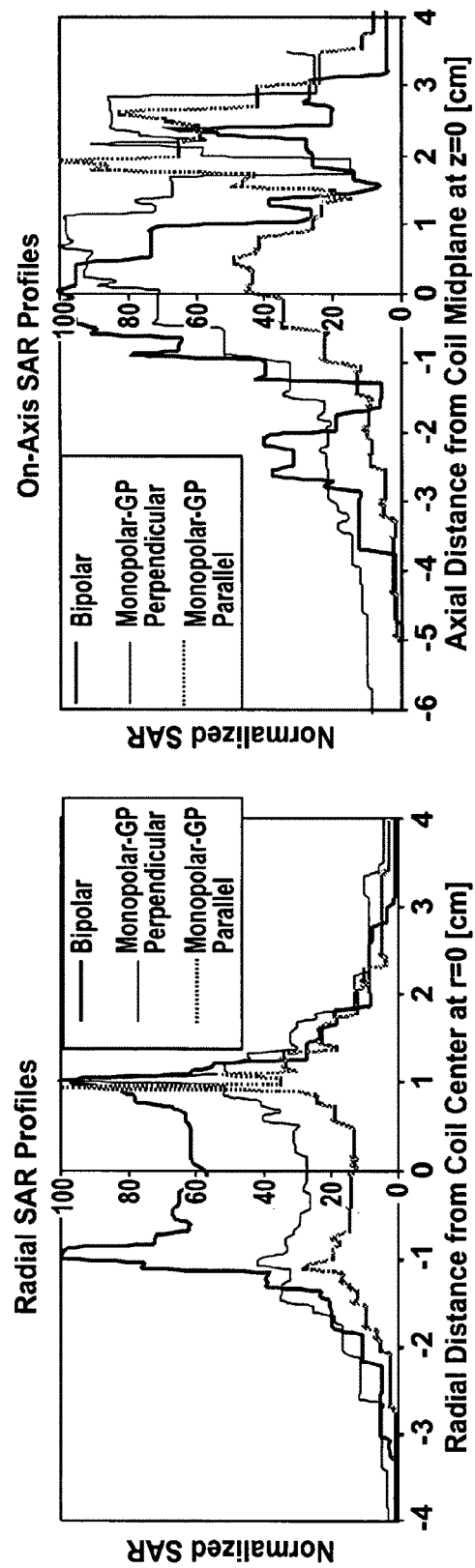
FIG. 19 shows plots of radial SAR profiles (left plot) and axial SAR profiles (right plot) for the test coil configurations specified in FIG. 17.
Figure 20:
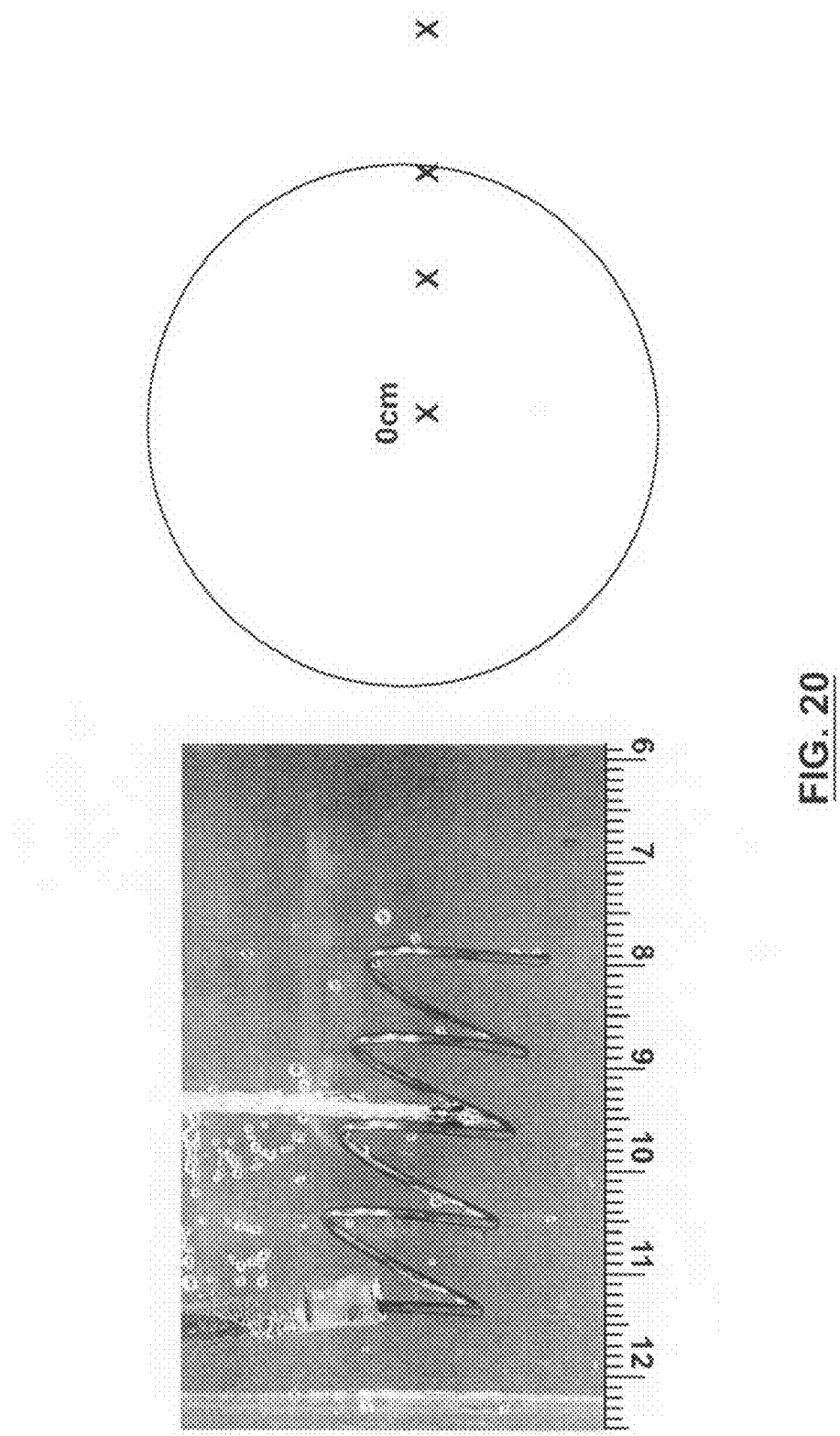
FIG. 20 shows a Monopolar Nitinol test coil cast in a polyacrylamide bovine serum albumin phantom (left) with a coaxial cable connected at the left end of the coil and temperature probes situated at the test coil mid-plane, at selected radial positions from the coil center (r=0 cm) (right)

The numerical simulation results include electric field vector distributions on a coronal plane through the test coil center shown in FIG. 18, and radial and axial SAR profiles shown in FIG. 19. For FIG. 18, the results were plotted with the same number and size of vector points and electric field intensity is proportional to cone size. For FIG. 19, the radial SAR profile was plotted at the coil mid-plane, and for on-axis profiles, the axial mid-plane of each test coil was located at z=0 cm, with the top and bottom of the test coil located at ±2 cm respectively. The ground plane (GP) (not shown) was located perpendicular and parallel to the test coil axis 7 cm from the end or edge of the test coil respectively. For both monopolar test coils, electric field intensity was greater towards the source end (top end) of the test coil. This was confirmed with the axial SAR profiles, which showed a decrease in power deposition towards the open end of the test coil. Radial SAR profiles showed a 30% to 40% drop in the central SAR for the monopolar test coils. Results for the ground plane parallel to the coil axis demonstrated the most dramatic deterioration of radial and axial SAR uniformity.

FEMLAB® was used to calculate the SAR profiles of monopolar test coils with different geometries to determine if variations in radius, pitch and length could improve the uniformity of the SAR inside the test coil. Test coils with different diameters (1-2 cm), pitch values (0.75-1.25 cm) and coil lengths (2.5-4 cm) were investigated (see Table 2). The end of the coil was 6 cm from the ground plane, with the axis of the coil perpendicular to ground. To validate the numerical model, SAR was measured for each test coil, made from Nitinol and cast in a polyacrylamide/bovine serum albumin phantom, and compared with calculated SAR. A coaxial cable is connected at the left end of the test coil. The SAR was measured using four non-electrically perturbing fluoroptic temperature probes (Model 3100SMM, Luxtron, Santa Clara, Calif.) located at selected radial positions from the coil center (r=0 cm) at the test coil mid-plane perpendicular to the test coil axis (see FIG. 20). For each test coil, inductance was calculated according to equation (6) (Lorrain and Corson 1962).

$$L = K \cdot \frac{N\Phi}{I} = K \cdot \frac{\mu_o N^2}{l} \cdot \pi R^2 \qquad (6)$$

where $\mu_o$ is the permeability of free space ($1/(\epsilon_o c^2) = 4\pi \times 10^{-7}$ H/m), c is the velocity of an electromagnetic wave in free space, $\Phi$ is the magnetic flux (Wb), I is the current (A), N is the number of turns, l is the coil length (m), R is the coil radius (m), and K is a factor used to calculate inductance of a short solenoid. Inductance depends on the geometry of the circuit and can be related to the line integral of the electric field around a path according to Faraday's induction law (see equation 7).

$$\oint E \cdot dl = -\frac{d\Phi}{dt} = -L\frac{dI}{dt} \qquad (7)$$

TABLE 2

Summary of coil geometries investigated using numerical simulations
(D = coil diameter, P = coil pitch, l = coil length)

| | Coil Parameters | | | | |
|---|---|---|---|---|---|
| | D (cm) | P (cm) | L (cm) | L (μH) | Wire Length (m) |
| I | 2 | 1 | 4 | 0.13 | 0.251 |
| II | 1.5 | 0.75 | 3 | 0.097 | 0.188 |
| III | 2 | 1.4 | 4.2 | 0.069 | 0.188 |
| IV | 1 | 1 | 4 | 0.036 | 0.125 |

FEMLAB® was also used to calculate the SAR profiles of monopolar test coils with different geometries to determine the optimum radius, pitch and length to achieve uniformity of the radial and axial SAR profile inside the test coil. Based on the results from the previous simulations, the ground pad was oriented perpendicular to the test coil axis. Measured and calculated SAR at selected radial positions at the test coil mid-plane were compared to validate the numerical model. Good agreement between the normalized measured and calculated SAR for each test coil geometry was observed (see Table 3).

Figure 21:
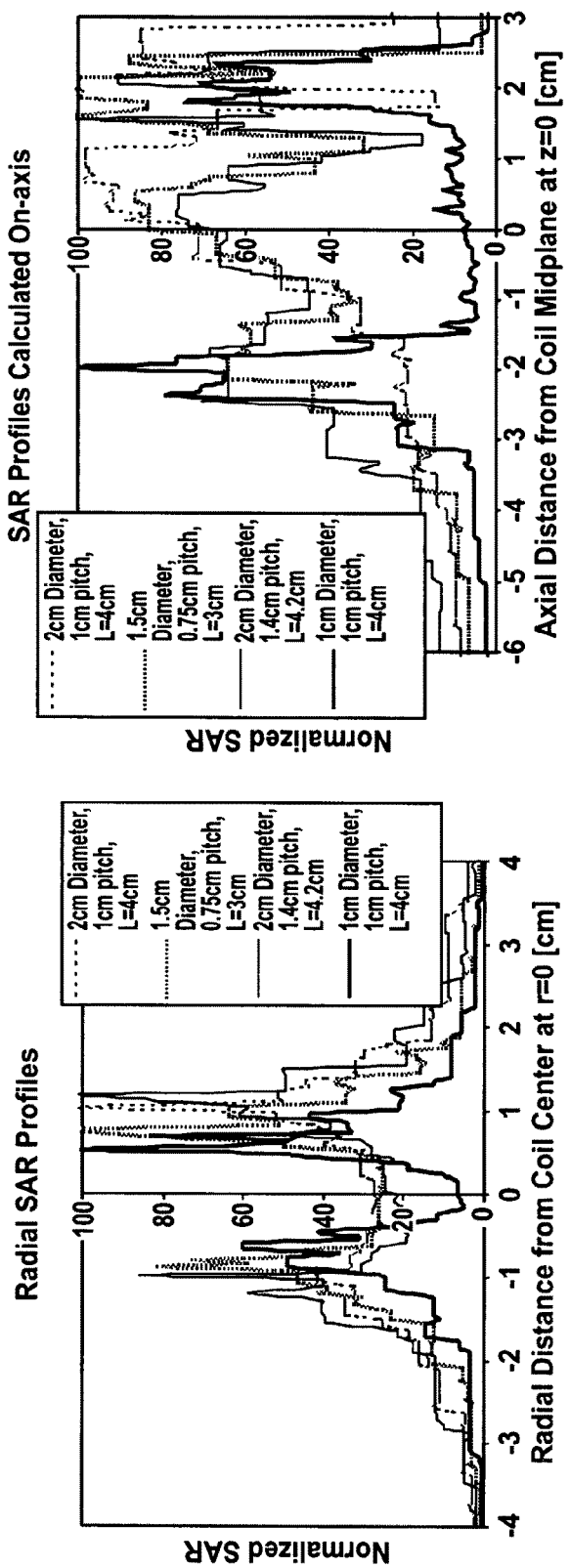
FIG. 21 shows radial SAR profiles (left) plotted at the monopolar test coil mid plane and axial SAR profiles (right) plotted on axis with the ground plane being perpendicular in both cases.

FIG. 21 shows radial SAR profiles (left) plotted at the test coil mid plane and axial SAR profiles plotted on axis (right), in which the axial mid-plane of each test coil was located at z=0 cm, and the ground plane was perpendicular to the test coil axis. FIG. 21 shows the calculated radial SAR profiles were comparable for coil geometries I, II and III with central SARs (r=0 cm) of 20%-30% relative to the SAR at the wire (r=1.0 cm) at the test coil mid-plane (z=0 cm). The 1 cm diameter test coil (coil IV) showed a central SAR less than 10% of the SAR at the wire (r=0.5 cm). For calculated axial SAR profiles, test coil I showed the largest decrease in power deposition towards the end of the test coil, which implies limited heating at the non-source test coil end. Test coils II and III showed the most uniform axial SAR profiles, which may improve heating along the length of the test coil. Test coil IV with a diameter of 1 cm showed large values of power deposition at either end of the test coil, 80-90% larger than in the middle of the test coil.

TABLE 3

Comparison of measured and calculated normalized SAR of monopolar test coils.

|  |  | Radial Positions | | | |
| --- | --- | --- | --- | --- | --- |
|  |  | 0 cm | 0.5 cm | 1.0 cm | 1.5 cm |
| Coil I | Experimental | 30% | 26% | 100% | 33% |
|  | Theoretical | 26% | 28% | 100% | 33% |

|  |  | Radial Positions | | | |
| --- | --- | --- | --- | --- | --- |
|  |  | 0 cm | 0.325 cm | 0.75 cm | 1.25 cm |
| Coil II | Experimental | 25% | 30% | 100% | 30% |
|  | Theoretical | 26% | 27% | 100% | 33% |

|  |  | Radial Positions | | | |
| --- | --- | --- | --- | --- | --- |
|  |  | 0 cm | 0.5 cm | 1.0 cm | 1.5 cm |
| Coil III | Experimental | 20% | 18% | 100% | 53% |
|  | Theoretical | 21.5% | 25% | 100% | 49% |

|  |  | Radial Positions | | | |
| --- | --- | --- | --- | --- | --- |
|  |  | 0 cm | 0.5 cm | 1.0 cm |  |
| Coil IV | Experimental | 4.3% | 100% | 19.95% | — |
|  | Theoretical | 6% | 100% | 25% | — |

Figure 22:
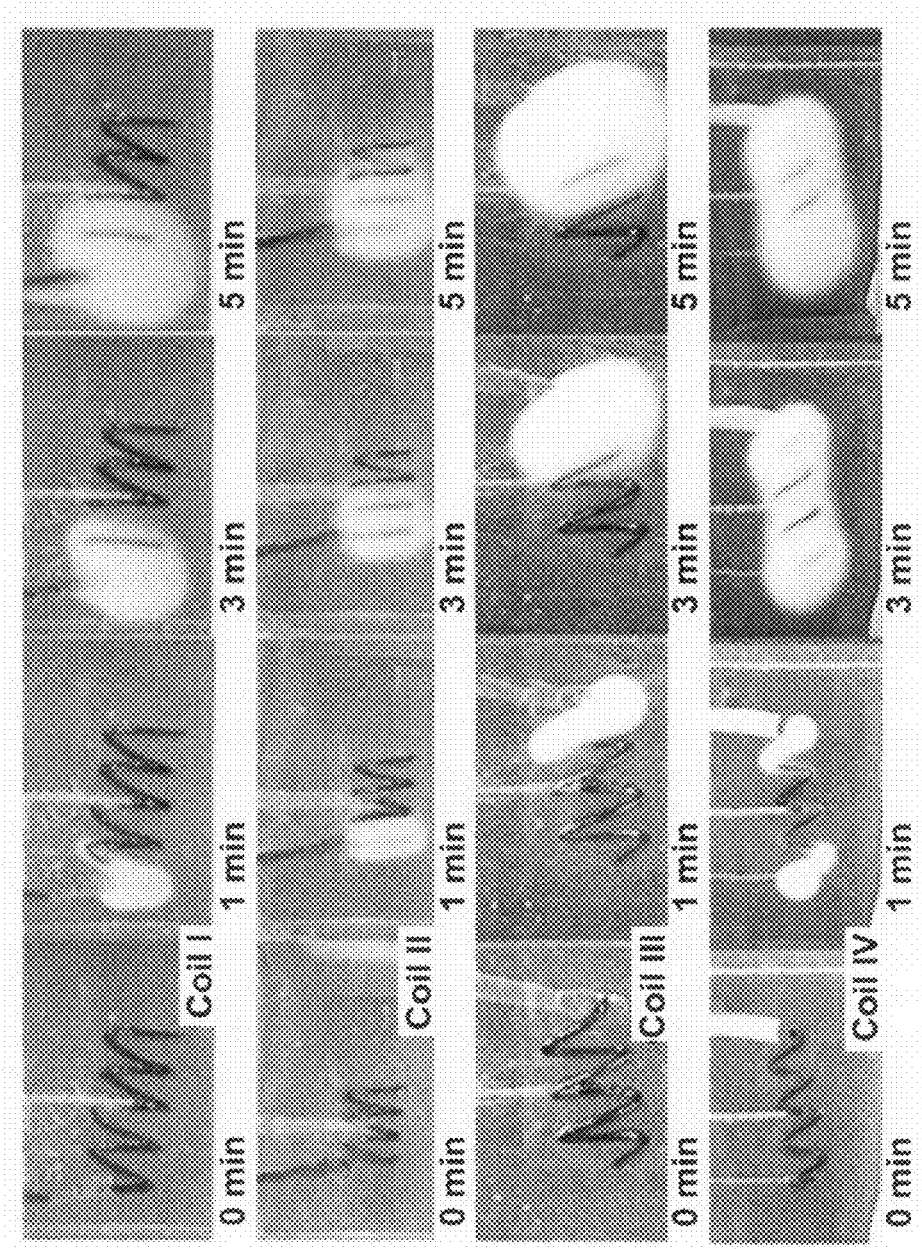
FIG. 22 shows a series of photographic images of coagulation patterns produced during a 5-minute heating period for a monopolar test coil cast in a polyacrylamide bovine serum albumin phantom.

For the phantom heating experiments, the details are similar to those described previously for the bipolar case. The monopolar test coils were connected at one end to a power source and terminated at the opposite end by an open circuit (a coaxial cable is connected at the left end (source) of test coil I and II, and to the right end of test coils III and IV). The test coil was operated at 27.12 MHz and was provided with an excitation signal having a power of 100 Watts. A ground pad (Valleylab, Boulder, Colo., USA) was also cast into the phantom, approximately 6 cm from the tip of the test coil and perpendicular to the test coil axis. Photographs of the time-dependent coagulation patterns were captured for each geometry following a 5-minute heating period. The images illustrated the nature of the power deposition patterns throughout the length of the test coils. FIG. 22 shows the images captured at 0 minutes, 1 minute, 3 minutes and 5 minutes for each test coil geometry. The white regions in the images indicate coagulation of the bovine serum albumin phantom which occurs when the phantom has reached a temperature of around 45° C. The phantom was approximately 20° C. before heating. The coagulation patterns were consistent with the calculated profiles. For larger test coils with longer wire lengths, coagulation was localized to the region of the test coil closest to the source. Test coils with shorter wire lengths show heating along the length of the coil.

Figure 23:
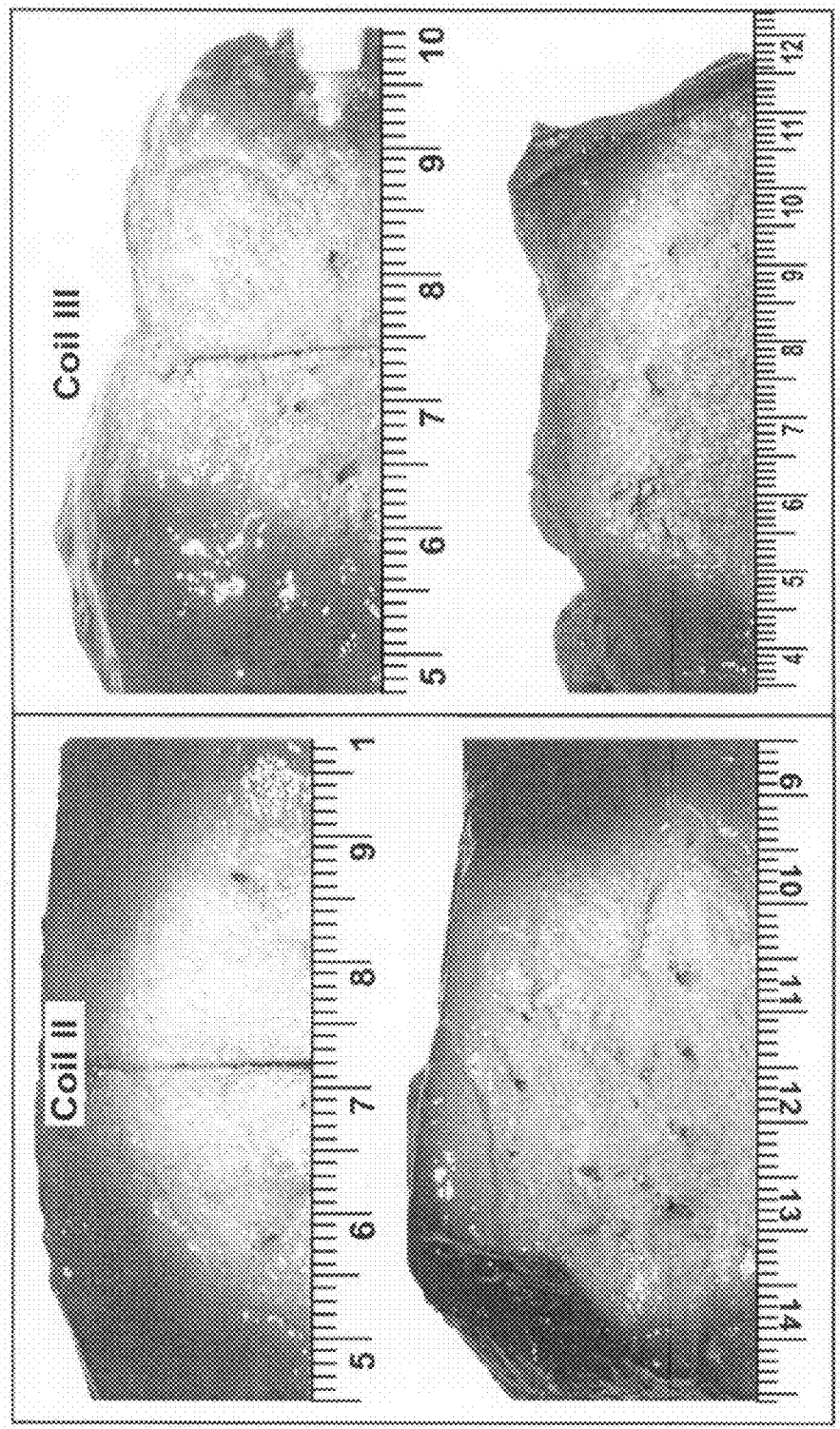
FIG. 23 shows photos of the coagulation of excised bovine liver using coil II (left) and coil III (right) specified in Table 2.

Coils II and III from Table 3 were evaluated in excised bovine liver. Liver was used because of the whitening of the treated region that can be visualized and measured. The test coils were operated at 27.12 MHz for 10 minutes with a net input power of 100 Watts using a 3325A Synthesizer/Function Generator (Hewlett-Packard, Loveland, Colo.) and an A-300 RF Power Amplifier (ENI, Rochester, N.Y.) via a flexible, unbalanced coaxial cable attached to one end of the test coil, and a series resonance and impedance matching circuit for maximum power delivery to the test coil. A ground pad electrode was positioned 7 cm from the end of the test coil and perpendicular to the coil axis. Test coil II produced an elliptical lesion 4 cm in diameter and 4.5 cm in length. Test coil III produced an elliptical lesion 3.5 cm in diameter and 6.5 cm in length (see FIG. 23). The lesion diameter (top photos) was measured through the test coil mid-plane perpendicular to the test coil axis. The lesion length (bottom photos) was measured along the length of the test coil through the test coil center. The lighter region is indicative of coagulation of the bovine liver.

The results of the test on the monopolar coil configuration showed that the external ground plane electrode acts as a dispersive electrode. Accordingly, the ground plane electrode perturbs the uniformity of the electric fields and SAR inside a monopolar coil compared to the bipolar coil. However, large (>3 cm) clinically useful coagulation patterns can still be produced when certain changes to the coil geometry are made, as discussed below. The test results also show that a ground plane results in the creation of numerous alternate currents paths, which limits the current in the RF coil electrode, the extent of which increases as one moves along the wire away from the source. This results in axial SAR profiles and coagulation patterns that are limited to a portion of the monopolar RF coil electrode nearest to the source. Changes to coil geometry which resulted in physically shorter wire lengths improved the heating pattern along the length of the monopolar RF electrode coil, but at the expense of the uniformity of the radial SAR profile inside the monopolar RF coil electrode. This may be explained by the second observation which indicates that in the presence of a ground plane, the overall effective current path length is increased, making the system much more susceptible to changes in wire length. Electrical length, which is defined as wire length/wavelength, is affected in turn. Decreasing electrical length can be achieved by reducing the coil wire length or increasing wavelength, via a reduction in frequency. Furthermore, the results achieved with changing wire lengths produced effects on the SAR similar to that observed with bipolar coils when changes to frequency were made. A reduction in frequency increases the static charge component of the electric field along the wire relative to the dynamic charge component of the electric field inside the coil, resulting in less uniform radial SAR profiles. Therefore, increasing the effective current path length by the addition of a ground plane produced an effect on the radial SAR similar to that observed with changing frequency. Changes to the uniformity of radial SAR profiles resulting from changes to coil wire length were also initially attributed to inductance changes which accompany geometry changes, although for geometrically similar bipolar coils, changes in the SAR showed little dependence on inductance. However, the monopolar coil is also shown to successfully create large coagulation volumes in both phantoms and excised bovine liver specimens.

The numerical simulations used to investigate the effect of ground pad distance on the uniformity of the radial and axial SAR profiles showed that doubling the distance from the end of the monopolar RF coil electrode to a ground plane positioned perpendicular to the coil axis, improved the uniformity of the radial SAR profile by approximately 20% in the coil center with a negligible change in the uniformity of the axial SAR profile plotted on-axis (results not shown). Increasing the distance to the ground plane further increases the effective current path length, which increases the electrical length of the circuit and produces an effect similar to that observed with increasing frequency. Accordingly, during the heating of tumors, it may be beneficial to position the ground electrode a minimum of 14 cm from the monopolar RF coil electrode open end and perpendicular to the coil axis in order to improve the uniformity of the SAR and the resulting coagulation patterns.

The tests with the monopolar RF coil electrodes showed that good radial and axial uniformity in power deposition can be achieved with a 0.75 cm pitch and 3 cm length for a 1.5 cm diameter coil, and a 1.4 cm pitch and 4.2 cm length for a 2 cm diameter coil (however other geometries can be used along with other values for operating parameters). These coils were able to produce lesions in excised bovine liver of 4 cm×4.5 cm and 3.5 cm×6.5 cm respectively. These results demonstrate that the interstitial application of the monopolar RF coil electrode induction can heat large tumors using a single applicator delivered through a single needle insertion.

Figure 24:
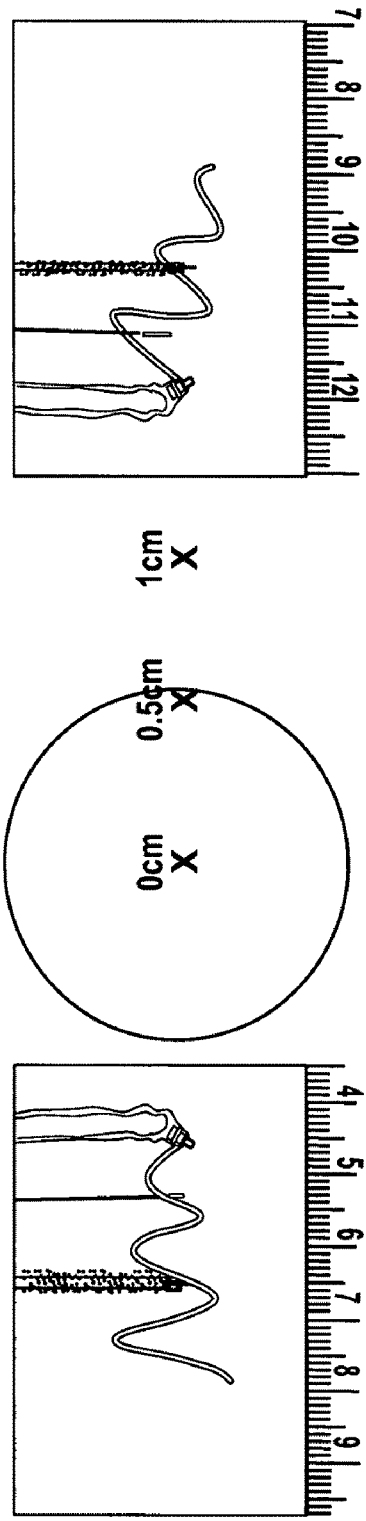
FIG. 24 shows a tapered monopolar coil electrode cast in a phantom with the left coil being connected to a coaxial cable at the tapered end and the right coil having a tapered opened end, along with fluoroptic temperature probes inserted at various positions (middle frame)

The SARs of monopolar RF coil electrodes that are tapered were also investigated using phantom models, with the ground plane perpendicular to the coil axis. The tapered coil that was tested was 4 cm in length with a 1 cm pitch and a diameter ranging from 0.5 cm at the small end to 2 cm at the large end. Two tapered monopolar configurations were tested: 1) the monopolar coil was tapered at the end corresponding to the source input and 2) the monopolar coil was tapered at the open end. In both cases, SAR was measured at the test coil mid-plane at radial positions of 0 cm, 0.5 cm and 1.0 cm from the coil center, and 1 cm from the source feed on-axis ($r=0$ cm) as shown in FIG. 24. The monopolar tapered coil on the left has a coaxial cable connected to the tapered end and the monopolar tapered coil on the right has a tapered opened end. Three fluoroptic temperature probes were inserted at the coil mid-plane ($z=0$ cm), at radial positions of 0 cm, 0.5 cm and 1.0 cm from the coil center ($r=0$ cm). A fourth probe was positioned on-axis, 1 cm from the feed. The diagram in the middle shows the radial position of the temperature probes at the mid-plane of the tapered coils. The probe at 0.5 cm is approximately 0.5 mm from the wire.

Figure 25:
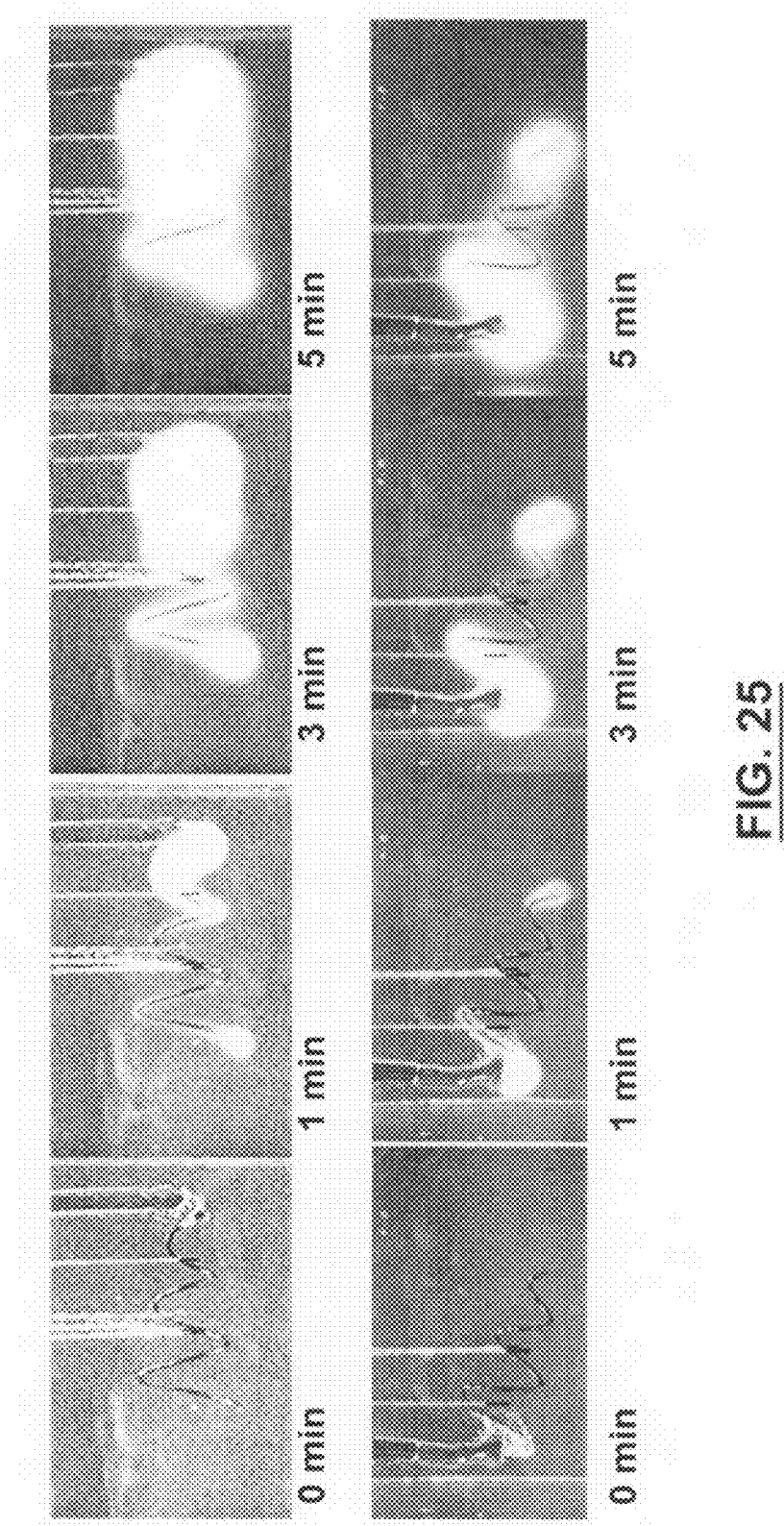
FIG. 25 shows photographic images of coagulation patterns of tapered monopolar RF electrode coils during a 5-minute heating period with the images being acquired at 0 minutes, 1 minute, 3 minutes and 5 minutes.

FIG. 25 shows photos illustrating the nature of the coagulation patterns produced using coils tapered at the source end and tapered at the open end. The images were acquired during a 5 minute heating period with the images being acquired at 0 minutes, 1 minute, 3 minutes and 5 minutes. Both tapered monopolar coil geometries showed coagulation at the ends first, which then progressed towards the middle. The coil tapered at the source end produced a cylindrical or elliptical shaped coagulation pattern, while the coil tapered at the open end produced an irregularly shaped tapered coagulation pattern. SAR from the tapered coils was measured at the coil mid-plane ($z=0$ cm) at radial positions form the coil center at $r=0$ cm and 1 cm from the source on-axis ($r=0$ cm) (see Table 4).

TABLE 4

Measured Normalized SAR of Monopolar Tapered Coils.

| | Radial Positions | | | |
|---|---|---|---|---|
| | $z=1$ cm, $r=0$ cm | $z=0$ cm, $r=0$ cm | $z=0$ cm, $r=0.5$ cm | $z=0$ cm, $r=1.0$ cm |
| Taper at Source End | 26.6% | 6.8% | 100% | 27.5% |
| Taper at Open End | 6.9% | 5% | 100% | 12.1% |

The tapered coils showed heating along the coil length and an SAR in the coil center of 5-7% compared to the SAR near the wire at the same axial position. The coil tapered at the source end produced a more uniform coagulation pattern lengthwise. In the presence of a ground plane, the eddy current losses in the outer turn at the source end are greater than at the open end because the current towards the end of the wire forming the coil has been significantly reduced (Elkamchouchi and Salem 2001). A smaller coil diameter at the source end reduced the extent of the eddy current losses at the feed (Ryff 1972) in order to offset the asymmetrical coagulation patterns produced along the coil length.

As previously mentioned, the power deposition pattern characteristic of conventional RF ablation electrodes operated around 500 KHz, which due to negligible coupling between the electric and magnetic fields at this frequency, results in a current density confined to the region immediately surrounding the conductor. Coagulation in regions not encompassed by the power deposition pattern (or SAR pattern) relies on thermal conduction, which is not always adequate to ensure therapeutic heating throughout the target volume, particularly in highly perfused areas.

In fact, perfusion has been shown to limit the therapeutic efficacy of high temperature thermal therapy in a number of high temperature thermal therapy applications. Tamaki et al (2004) showed that lesion size decreased in a porcine liver treated with a 460 kHz, 10-hook needle electrode, when in the presence of large vessels compared to regions without vessels. Burdio et al (2003) tested a 480 kHz radiofrequency needle electrode in the liver of 24 adult female farm pigs and showed that the mean lesion volume achieved using radiofrequency ablation with vascular inflow occlusion was much larger than those produced without occlusion.

Tests were also conducted on a porcine model with the RF electrode geometry and operating frequencies described herein to evaluate the feasibility of the RF applicator 22 in a perfused environment. The pig is the only large animal that is reasonably comparable to humans. Many studies testing radiofrequency ablation devices have used pig models because of the similarity in organ size and anatomy. In a study, Wright (2005) compared radiofrequency ablation to microwave ablation in a hepatic porcine model showing that microwave thermal therapy was less affected by the presence of blood vessels. He showed that on average, radiofrequency ablation was deflected by 26% in the presence of local blood vessels while microwave ablation was deflected by only 4%. Crowley et al (2001) and Rendon et al (2001) used an in-vivo porcine model to evaluate the efficacy of radiofrequency ablation in renal tissue. Rendon et al concluded that in a highly perfused organ such as the kidney, renal blood flow is an efficient cause of heat loss by convection. They showed that lesions were wedge shaped as opposed to the desired spherical shaped lesions and lesion size was not reproducible.

Permission from the University Health Network Animal Resource Center ethical committee under guidelines set by the Canadian Council of Animal Care was obtained prior to the initiation of these experiments. In an acute study, the interstitial radiofrequency helical coil was tested in two male Yorkshire pigs weighing 60 kg (Pig 1) and 80 kg (Pig 2). A general 2.5% isoflurane anesthetic was administered to the animals with 2300 mg of ketamine hydrochloride induction. The kidneys and the liver of the animals were exposed through a midline incision and treated separately with the RF coil applicator, which was inserted under direct vision and ultrasound guidance. B-Scan Ultrasound images of porcine kidney were taken when the radiofrequency coil applicator was inserted into the animals. Increased backscattered signal intensity was seen which denoted coil windings. Three out of four of the turns of the coil were visible in the images.

The animals were sacrificed immediately after treatment. During treatment blood pressure was monitored using an external manometer, and pulse rate and oxygen saturation were measured using a pulse oximeter. Kidneys and the liver were harvested immediately after sacrifice. The abdominal cavity was inspected for thermal damage to the surrounding structures and evidence of other unsuspected complications. The kidneys and livers were prepared for gross and histological examination. Dimensions and shapes of the lesions were recorded and representative sections of the lesions were fixed in 10% formalin and stained with hematoxylin-eosin (H&E) for examination of morphology and immunohistochemical Tunnel staining.

During RF treatment, the liver and kidney tissues were heated with a helical coil applicator 1 cm in diameter, 4 cm in length with a pitch of 1 cm. This coil size was selected based on the pigs' organ size, which were not large enough for treatment by larger coils. The coil was driven with 100 Watts at 27.12 MHz using a signal generator (10 kHz-1000 MHz Model 52022-910E, Marconi Instruments Ltd), a 0.3-35 MHz power amplifier (Model A150, Rochester N.Y.) a flexible, unbalanced coaxial cable attached to the proximal end of the RF coil electrode, and a series resonance and impedance matching circuit for maximum power delivery to the coil. A dispersive electrode required to complete the current path, was affixed to the lateral abdomen on the right side of the pig. The liver and kidney of Pigs 1 and 2 were heated for 20 minutes and 13 minutes respectively. Non-electrically perturbing fluoroptic temperature probes were placed inside the tissue-loaded coil on-axis (r=0 cm) for remote thermometry at locations T1 (proximal end), T2 (middle), and T3 (distal end) as shown in FIG. 26.

Figure 27:
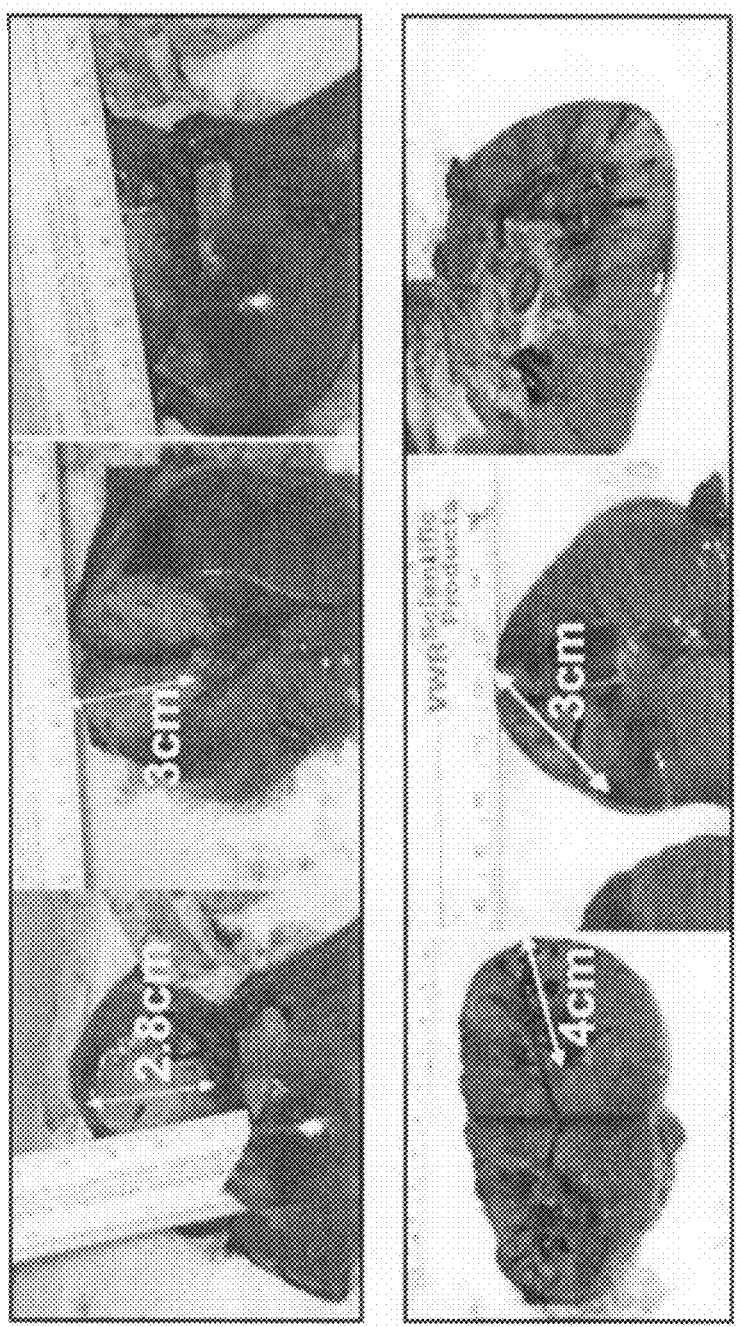
FIG. 27 shows gross examination of liver lesion (top row) and kidney lesion (bottom row) after RF coil ablation at 27.12 MHz.

A total of 2 lesions were produced, one in the liver of Pig 1 and the other in the right kidney of Pig 2, with a 1 cm diameter, 4 cm length, 4 turn coil operated at 27.12 MHz. FIG. 27 shows gross examination of liver lesion (top row) and kidney lesion (bottom row) after RF coil ablation at 27.12 MHz. Whitening is indicative of coagulation or denaturation of the structural proteins. The gross findings show an almost spherical lesion 3 cm×2.8 cm×2.8 cm in the liver, and a wedge-shaped lesion 4 cm in length and 3 cm in width in the kidney. The base of the renal lesion is in the medulla and the apex is in the cortex. The whitening of the tissue indicates thermal lesions in liver and kidney. Temperatures were measured in real-time during heating and are reported as temperature rise in FIG. 28. The RF ablation of normal porcine liver is shown on the left and porcine kidney tissue is shown on the right. Denaturation of structural proteins occurs at temperatures greater and equal to 55° C. The initial temperature of the animal was 35° C. Absolute temperatures in excess of 70° C. and 100° C. were observed in the liver and kidney respectively. These results show that the RF electrode and heating technique described herein works for in-vivo heating of tissue in highly perfused environments.

In alternative embodiments, one or more changes can be made to the RF tissue ablation apparatus 10 or the coil electrode 24 to prevent damage to the coil electrode 24. For example, the coil electrode 24 can be internally cooled to limit the current density along the wire when high powers are needed. In these instances, the internal cooling prevents very high temperatures and charring of the coil electrode 24. Alternatively, or in addition, the signal generator 16 can be operated to provide the excitation current in a pulsed manner to limit the current density in the coil electrode 24 to a safe level to avoid charring of the coil electrode 24, while at the same time maintaining the required temperature increase in the tissue that is needed for tissue ablation. Alternatively, or in addition, the coil electrode 24 can include ferromagnetic seeds placed on-axis, i.e. the ferromagnetic seeds are placed in a parallel fashion with regards to the longitudinal axis of the coil electrode 24 and in a middle or central region of the coil electrode 24. This enhances heating of the tissue in the vicinity of the middle regions of the coil electrode 24, where there can be high perfusion, while reducing the amount of RF power that is needed, which also helps avoid charring of the coil electrode 24. The ferromagnetic seeds can be placed in the coil electrode 24 in a uniform fashion; for example, one seed can be placed per centimeter for a mid-portion of the coil electrode 24.

In one aspect, at least one embodiment described herein provides an apparatus for heating a target tissue region. The apparatus comprises: a control unit for controlling the operation of the apparatus, the control unit including a user interface adapted for allowing a user to use the apparatus; a signal generator coupled to the control unit, the signal generator being adapted for generating an excitation current having a frequency in the range of about 5 to 50 MHz; a power amplifier coupled to the signal generator for amplifying the excitation current; an impedance matching circuit coupled to the power amplifier for reducing impedance mismatch; and an applicator coupled to the impedance matching circuit, the applicator including a single, helical coil electrode for application to the target tissue to heat the target tissue when provided with the excitation current.

In at least some cases, the applicator can further comprise a non-conductive cannula, and a deployment mechanism adapted for inserting the coil electrode into the target tissue when actuated.

Accordingly, the coil electrode can be made with a shape memory alloy that has a non-deployed state when housed within the cannula, and a deployed state when moved out of the cannula by the deployment mechanism.

The shape memory alloy may comprise Nitinol.

The applicator may comprise a temperature sensor for sensing the temperature of the region surrounded by the coil electrode.

The coil electrode may have a tightly wound helical geometry.

The coil electrode may have a loosely wound helical geometry.

The coil electrode may have a tapered coil geometry.

The coil electrode may have a length of about 1 to 6 cm.

The coil electrode may have a diameter of about 0.5 to 3 cm.

The coil electrode may have a pitch of about 0.5 to 2 cm.

The coil electrode may have a major dimension that is at least 50% larger than the minor dimension.

The coil electrode may have an aspect ratio of about 2 to 4.

The coil electrode may have a wire thickness of about 0.5 to 1.25 mm.

The coil electrode may be connected in a bipolar configuration.

For bipolar configurations, the applicator may comprise a first needle having a wire connected to a first region of the coil electrode to provide the excitation current, and the apparatus may further comprise a second needle adapted for coupling with a second region of the coil electrode to provide a ground connection with the signal generator.

The coil electrode may be connected in a monopolar configuration, and have a source end portion for receiving the excitation current, and the apparatus further comprises at least one ground electrode for attachment to the signal generator and a remote tissue surface with respect to the target tissue region.

For the bipolar configuration, the coil electrode may have an electrical length of about 20 to 25% of the wavelength of the excitation current.

The impedance matching circuit may comprise a transformer, and a network of inductors and capacitors.

The transformer may be a step-down transformer, the network may include an inductor connected in series with a capacitor, and the transformer is connected in series with the network.

The apparatus may provide the excitation current applied to the coil electrode with a power level of about 20 to 500 Watts.

In at least some cases, the coil electrode is internally cooled.

In at least some cases, the signal generator is configured to pulse the excitation current to limit current density in the coil electrode.

In at least some cases, the coil electrode comprises ferromagnetic seeds placed parallel to a longitudinal axis of coil electrode and in a mid-region of the coil electrode.

In another aspect, at least one embodiment described herein provides a method of heating a target tissue region of a patient. The method comprises: applying a single, helical coil electrode at the target tissue region; generating an excitation current with a frequency sufficient for magnetic induction to generate an axial electric field within the volume surrounded by the coil electrode; and applying the excitation current to the coil electrode.

The method further comprises generating the excitation current with a frequency low enough to minimize attenuation of the generated electric and magnetic fields and to minimize any opposing induction fields set up by the induced eddy currents in the coil electrode.

The method may further comprise generating the excitation current with a frequency in the range of about 5 to 50 MHz.

The method may further comprise housing the coil electrode in an applicator as defined above.

The method may further comprise selecting properties for the coil electrode as defined above.

In another aspect, at least one embodiment described herein provides an electrode arrangement for heating a target tissue region of a patient. The electrode arrangement comprises a single coil electrode for application at the target tissue region, wherein the coil electrode is adapted to produce an axial electric field within the volume surrounded by the coil electrode when provided with an excitation current having a frequency in the range of 5 to 50 MHz.

In another aspect, at least one embodiment described herein provides an electrode arrangement for heating a target tissue region of a patient. The electrode arrangement comprises a single coil electrode having a helical geometry and arranged to be operated with a time-varying current source at a frequency sufficient for magnetic induction, the time-varying current source produces a circumferential electric field and a secondary axially directed electric field, within the volume surrounded by the coil electrode, the secondary axially directed electric field arising from the charge distribution along the coil electrode.

In another aspect, at least one embodiment described herein provides for use of an electrode arrangement as defined above for heating tissue.

It should be understood that various modifications can be made to the embodiments described and illustrated herein, without departing from the invention, the scope of which is defined in the appended claims.

REFERENCES

Beaugrand M, N'kontchou G, Seror O, Ganne N and Trinchet J C, Local/Regional and systemic treatments of hepatocellular carcinoma. *Seminals of Liver Disease*. 2005. 25, 201-211.

Brezovich I A, Young J H and Wang M T, Temperature distributions in hyperthermia by electromagnetic induction: A theoretical models for the thorax. *Medical Physics*. 1983. 10 57-65.

Burdio F, Guemes A, Burdio J M, Navarro A, Sousa R. et al, Large Hepatic Ablation with Bipolar Saline-Enhanced Radiofrequency: AN Experimental Study in in Vivo Porcine Liver with a Novel Approach. Journal of Surgical Research. 2003 Vol. 110 pp 193-201.

Chiba T, Tokuuye K, Matsuzaki Y, Sugahara S, Chuganji Y, Kagei K, Shoda J, Hata M, Abei M, Igaki H, Tanaka N and Akine Y, Proton Beam Therapy for Hepatocellular Carcinoma: A retrospective review of 162 patients. *Clinical Cancer Research,* 2005.11, 3799-3805.

Chin L and Sherar M, Changes in dielectric properties of ex-vivo bovine liver at 915 MHz during heating, *Physics in Medicine and Biology*. 2001. 46 197-211.

Chute F S and Vermeulen F E, A Visual Demonstration of the Electric Field of a Coil Carrying a Time-Varying Current. *IEEE Transactions on Education*. 1981. E-24 278-283.

Crowley J D, Shelton J, Iverson A J, Burton M P, Dalrymple N C and Bishoff J T, Laparoscopic and compute-tomography-guided percutaneous radiofrequency ablation of renal tissue: acute and chronic effects in an animal model. Urology. 2001. Vol. 57 pp 976-980.

Duerig T W, Melton K N, Stöckel D, Wayman C M, Engineering Aspects of Shape Memory Alloys. Bufterworth-Heinemann Ltd., Toronto, ©1990.

Elkamchouchi H M and Salem A L, Helical Antennas with nonuniform diameter. *Eighteenth National Radio Science Conference*. March 2001.143-152.

Guerquin-Kern J L, Hagmann M J, Levin R L, Experimental Characterization of Helical Coils as hyperthermia Applicators. *IEEE Transactions on Biomedical Engineering*. 1988. BME-35 46-52.

Iskander M F and Tumeh A M, 1989, Design optimization of interstitial antennas. *IEEE Transactions on Biomedical Engineering,* 1989. 36 238-246.

Jemal A, Ward E, Samuels A, Tiwari R C, Ghafoor A, Feuer E J and Thun M J, Cancer Statistics 2005, *CA Cancer J Clin,* 2005.55 10-30.

Jordan E C and Balmain K G, Electromagnetic Waves and Radiating Systems $2^{nd}$ Ed. Prentice-Hall, Inc. © 1968, NJ.

Knoepfel H, Magnetic fields: a comprehensive theoretical treatise for practical use. Wiley © 2000, Toronto.

Kong F M, Ten Haken R K, Schipper M J, Sullivan M A, Chen M, Lopez C, Kalemkerian G P and Hayman J A, High-dose radiation improved local tumor control and overall survival in patients with inoperable/unresectable non-small-cell lung cancer: Long-term results of a radiation dose escalation study, *Int. J. Radiation Oncology Biol. Phys.* 2005. 63 No. 2 324-333.

Kumaradas J C and Sherar M D, An edge-based finite element model of microwave heating in hyperthermia: method and verification. 2002. *International Journal of Hyperthermia*. 18 426-440.

Lagerwaard F J, Senan S, Van Meerbeck J P, Graveland W J, Has 3-D conformal radiotherapy (3D CRT) improved the local tumor control for stage I non-small cell lung cancer? *Radiotherapy & Oncology*. 2002. 63 151-157.

Lorrain P and Corson D, Electromagnetic Fields and Waves. W. H. Freeman and Company, © 1962, New York.

McGahan J P and Dodd G D, Radio frequency Ablation of the Liver: Current Status. *AJR.* 2001. 176 3-16.

McLoud T C, Lung Cancer: Imaging techniques for diagnosis and staging of lung cancer, *Clinics in Chest Medicine,* 2002. 23 No. 1.

McDonald, M, Lochhead S, Chopra R and Bronskill M J, Multi-modality tissue-mimicking phantom for thermal therapy. *Physics in Medicine and Biology.* 2004. 49 2767-2778.

Moore L E, Wilson R T and Campleman S L, Lifestyle factors, exposures, genetic susceptibility, and renal cell cancer risk: a review. *Cancer Invest.* 2005. 23 240-255.

Mountain C F, Revisions in the international system for staging lung cancer. *Chest,* 1997.11 1710-1717.

Namjoshi K V and Biringer P P, Multiple conductor induction problem: Analytical approach. *American Institute of Physics.* 1990. 67 4732-4734.

Namjoshi K V and Biringer P P, Multiple conductors in transverse magnetic field and their application in magnetic shielding. *IEEE Transactions on Magnetics.* 1991. 27 3916-3919.

Rendon R A, Gertner M R, Sherar M D, Asch M R, Kachura J R, Sweet J and Jewett M A S, Development of a radio frequency based thermal therapy technique in an in-vivo porcine model for the treatment of small renal masses. *The Journal of Urology.* 2001.166 292-298.

Ryan T P, Mechling J A and Strohbehn J W, Absorbed power deposition for various insertion depths for 915 MHz interstitial dipole antenna arrays: experiment versus theory. *Int J Radiation Oncology Biol. Phys.* 1990. 19 377-387.

Ryff P F, Current Distribution in Helical Solenoids, *IEEE Transactions on Industry Applications.* 1972. 8 485-490.

Stöckel D, Nitinol Medical Devices and Implants. *SMST-2000 Conference Proceedings,* 2001.

Stuchly M A and Stuchly S S, Coaxial Line Reflection methods for Measuring Dielectric Properties of Biological Substances at Radio and Microwave Frequencies—A review. *IEEE Trans. Instrum. Meas.* 1980.

Stuchly M A and Stuchly S S, Measurement of Radio Frequency Permittivity of Biological Tissues with an Open-Ended Coaxial Line: Part I. *IEEE Transactions on Microwave Theory and Techniques.* 1982. 30 82-86.

Stuchly M A and Stuchly S S, Dielectric Properties of Biological Substances-Tabulated. *Journal of Microwave Power.* 1980.15 20-25.

Tamaki K, Shimizu I, Oshio A, Fukano H, Inoue H et al. Influence of large intrahepatic blood vessels on the gross and histological characteristics of lesions produced by radiofrequency ablation in a pig liver model. Liver International. 2004. Vol. 24 pp. 696-701.

Wright A S, Sampson L A, Warner T F, Mahvi D M, Lee F T, Radiofrequency versus Microwave Ablation in a Hepatic Porcine Model. Radiology. 2005. Vol. 236 pp 132-139.

Varkarakis I M, Allaf M E, Inagaki T, Bhayani S B, Chan D Y, Su L M, Jarreft T W, Kavoussi L R and Soloman S B, Percutaneous radio frequency ablation of renal masses: results at a 2 year mean follow-up. *The Journal of Urology,* 2005.174 456-460.

The invention claimed is:

1. An apparatus for heating a target tissue region, wherein the apparatus comprises:
    a) a control unit for controlling the operation of the apparatus, the control unit including a user interface adapted for allowing a user to use the apparatus;
    b) a signal generator coupled to the control unit, the signal generator being adapted for generating an excitation current having a frequency in the range of about 5 to 50 MHz;
    c) a power amplifier coupled to the signal generator for amplifying the excitation current;
    d) an impedance matching circuit coupled to the power amplifier for reducing impedance mismatch; and
    e) an applicator coupled to the impedance matching circuit, the applicator including a single, helical coil electrode for application to the target tissue to heat the target tissue when provided with the excitation current.

2. The apparatus of claim 1, wherein the applicator further comprises a non-conductive cannula, and a deployment mechanism adapted for inserting the coil electrode into the target tissue when actuated.

3. The apparatus of claim 2, wherein the coil electrode is made with a shape memory alloy and has a non-deployed state when housed within the cannula, and a deployed state when moved out of the cannula by the deployment mechanism.

4. The apparatus of claim 3, wherein the shape memory alloy comprises Nitinol.

5. The apparatus of claim 1, wherein the applicator comprises a temperature sensor for sensing the temperature of the region surrounded by the coil electrode.

6. The apparatus of claim 1, wherein the coil electrode has a tightly wound helical geometry.

7. The apparatus of claim 1, wherein the coil electrode has a loosely wound helical geometry.

8. The apparatus of claim 1, wherein the coil electrode has a tapered coil geometry.

9. The apparatus of claim 1, wherein the coil electrode has a length of about 1 to 6 cm.

10. The apparatus of claim 1, wherein the coil electrode has a diameter of about 0.5 to 3 cm.

11. The apparatus of claim 1, wherein the coil electrode has a pitch of about 0.5 to 2 cm.

12. The apparatus of claim 1, wherein the coil electrode has a minor dimension and a major dimension that is at least 50% larger than the minor dimension.

13. The apparatus of claim 1, wherein the coil electrode has an aspect ratio of about 2 to 4.

14. The apparatus of claim 1, wherein the coil electrode has a wire thickness of about 0.5 to 1.25 mm.

15. The apparatus of claim 1, wherein the coil electrode is connected in a bipolar configuration.

16. The apparatus of claim 15, wherein the applicator comprises a first needle having a wire connected to a first region of the coil electrode to provide the excitation current, and the apparatus further comprises a second needle adapted for coupling with a second region of the coil electrode to provide a ground connection with the signal generator.

17. The apparatus of claim 1, wherein the coil electrode is connected in a monopolar configuration, and has a source end portion for receiving the excitation current, and the apparatus further comprises at least one ground electrode for attachment to the signal generator and a remote tissue surface with respect to the target tissue region.

18. The apparatus of claim 17, wherein the coil electrode has an electrical length of about 20 to 25% of the wavelength of the excitation current.

19. The apparatus of claim 1, wherein the impedance matching circuit comprises a transformer, and a network of inductors and capacitors.

20. The apparatus of claim 19, wherein the transformer is a step-down transformer, the network includes an inductor connected in series with a capacitor, and the transformer is connected in series with the network.

21. The apparatus of claim 1, wherein the apparatus provides the excitation current applied to the coil electrode with a power level of about 20 to 500 Watts.

22. The apparatus of claim 1, wherein the coil electrode is internally cooled.

23. The apparatus of claim 1, wherein the signal generator is configured to pulse the excitation current to limit current density in the coil electrode.

24. The apparatus of claim 1, wherein the coil electrode comprises ferromagnetic seeds placed parallel to a longitudinal axis of the coil electrode and in a mid-region of the coil electrode.

25. A method of heating a target tissue region of a patient, wherein the method comprises:
   applying a single, helical coil electrode at the target tissue region;
   generating an excitation current with a frequency sufficient for magnetic induction to generate an axial electric field within the volume surrounded by the coil electrode; and
   applying the excitation current to the coil electrode.

26. The method of claim 25, wherein the method further comprises generating the excitation current with a frequency low enough to minimize attenuation of the generated electric and magnetic fields and to minimize any opposing induction fields set up by induced eddy currents in the coil electrode.

27. The method of claim 25, wherein the method further comprises generating the excitation current with a frequency in the range of about 5 to 50 MHz.

28. The method of claim 27, wherein the method further comprises employing a temperature sensor for sensing the temperature of the region surrounded by the coil electrode, and discontinuing the electric current if the temperature rises above an unsafe temperature.

29. The method of claim 27, wherein the method further comprises providing the excitation current applied to the coil electrode with a power level of about 20 to 500 Watts.

30. An electrode arrangement for heating a target tissue region of a patient, wherein the electrode arrangement comprises a single coil electrode for application at the target tissue region, wherein the coil electrode is adapted to produce an axial electric field within the volume surrounded by the coil electrode when provided with an excitation current having a frequency in the range of 5 to 50 MHz.

31. An electrode arrangement for heating a target tissue region of a patient, wherein the electrode arrangement comprises a single coil electrode having a helical geometry and arranged to be operated with a time-varying current source at a frequency sufficient for magnetic induction, wherein the time-varying current source produces a circumferential electric field and a secondary axially directed electric field, within the volume surrounded by the coil electrode, the secondary axially directed electric field arising from the charge distribution along the coil electrode.

32. Use of an electrode arrangement as claimed in claim 30 for heating tissue, wherein the use comprises:
   selecting a size of the coil electrode based on a type and size of the target tissue region;
   selecting an operating frequency to produce the axial electric field within the volume surrounded by the coil electrode during operation;
   selecting an amount of power for the current source;
   selecting a length of time for exposing the target tissue region to RF energy provided by the coil electrode during operation;
   applying the coil electrode to the target tissue region; and
   applying the excitation current to the coil electrode for heating the target tissue region.

33. Use of an electrode arrangement as claimed in claim 31 for heating tissue, wherein the use comprises:
   selecting a size of the coil electrode based on a type and size of the target tissue region;
   selecting an operating frequency to produce the axially directed electric field within the volume surrounded by the coil electrode during operation;
   selecting an amount of power for the current source;
   selecting a length of time for exposing the target tissue region to RF energy provided by the coil electrode during operation;
   applying the coil electrode to the target tissue region; and
   applying the current source to the coil electrode for heating the target tissue region.

* * * * *

UNITED STATES PATENT AND TRADEMARK OFFICE
CERTIFICATE OF CORRECTION

| | | |
|---|---|---|
| PATENT NO. | : 8,073,551 B2 | Page 1 of 1 |
| APPLICATION NO. | : 11/696550 | |
| DATED | : December 6, 2011 | |
| INVENTOR(S) | : Claire McCann and Michael D. Sherar | |

It is certified that error appears in the above-identified patent and that said Letters Patent is hereby corrected as shown below:

Title page, item (74) Attorney, Agent or Firm in the bibliographic details, "Bereskin & Park" should read --Bereskin & Parr--.

Signed and Sealed this
Tenth Day of April, 2012

David J. Kappos
*Director of the United States Patent and Trademark Office*